US010363230B2

(12) United States Patent
Sang et al.

(10) Patent No.: US 10,363,230 B2
(45) Date of Patent: *Jul. 30, 2019

(54) 6-SHOGAOL DERIVATIVES AND ACTIVITIES THEREOF

(71) Applicant: North Carolina Agricultural and Technical State University, Greensboro, NC (US)

(72) Inventors: Shengmin Sang, Concord, NC (US); Yingdong Zhu, Concord, NC (US)

(73) Assignee: North Carolina Agricultural and Technical State University, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/934,643

(22) Filed: Mar. 23, 2018

(65) Prior Publication Data

US 2018/0271804 A1 Sep. 27, 2018

Related U.S. Application Data

(60) Provisional application No. 62/475,440, filed on Mar. 23, 2017.

(51) Int. Cl.
| | | |
|---|---|---|
| *A61P 27/02* | (2006.01) | |
| *A61K 31/12* | (2006.01) | |
| *A61P 9/00* | (2006.01) | |
| *A61P 25/02* | (2006.01) | |
| *A61P 1/18* | (2006.01) | |

(52) U.S. Cl.
CPC ............... *A61K 31/12* (2013.01); *A61P 1/18* (2018.01); *A61P 9/00* (2018.01); *A61P 25/02* (2018.01); *A61P 27/02* (2018.01)

(58) Field of Classification Search
None
See application file for complete search history.

(56) References Cited

U.S. PATENT DOCUMENTS

| 7,528,143 B2 | 5/2009 | Noronha et al. |
| 9,272,994 B1 | 3/2016 | Sang et al. |
| 9,549,911 B2 | 1/2017 | Sang et al. |
| 2018/0280320 A1 | 10/2018 | Sang et al. |

OTHER PUBLICATIONS

Backstrom et al., "Synthesis of Some Novel Potent and Selective Catechol O-Methyltransferase Inhibitors," J. Med. Chem. 32, pp. 841-846 (1989).
Berge et al., "Pharmaceutical Salts," J. of Pharmaceutical Sciences, 66:1, pp. 1-19 (1977).
De Lucia et al., "Plant Catechols and Their S-Glutathionyl Conjugates as Antinitrosating Agents: Expedient Synthesis and Remarkable Potency of 5-S-Glutathionylpiceatannol," Chem. Res. Toxicol. 21:12, pp. 2407-2413 (2008). (Abstract, 2 pages).
Lambert et al., "Peracetylation as a Means of Enhancing in Vitro Bioactivity and Bioavailability of Epigallocatechin-3-Gallate," Drug Metab. Dispos. 34:12, pp. 2111-2116 (2006).
Sieber et al., "Asymmetric Ni-Catalyzed Conjugate Allylation of Activated Enones," J. Am. Chem. Soc. 130:14, 4978-4983 (2008).
Sieber et al., "Catalytic Conjugate Addition of Allyl Groups to Styryl-Activated Enones," J. Am. Chem. Soc. 129, pp. 2214-2215 (2007).
Tsujita, et al., "Nitro-fatty acids and cyclopentenone prostaglandins share strategies to activate the Keap1-Nrf2 system: a study using green fluorescent protein transgenic zebrafish," Genes Cells 16:1, 46-57 (2011).
Wakabayashi et al., "Protection against electrophile and oxidant stress by induction of the phase 2 response: Fate of cysteines of the Keap1 sensor modified by inducers," Proc. Natl. Acad. Sci. U.S.A. 101, 2040-2045 (2004).
Zhu et al "Metabolites of Ginger Component [6]-Shogaol Remain Bioactive in Cancer Cells and Have Low Toxicity in Normal Cells: Chemical Synthesis and Biological Evaluation," PLOS One, 8:1, e54677, pp. 1-13 (2013).
Zhu et al., "Synthesis, evaluation, and metabolism of novel [6]-shogaol derivatives as potent Nrf2 activators," Free Radical Biology and Medicine, vol. 95, pp. 243-254 (2016).
De Lucia et al., "Plant Catechols and Their S-Glutathionyl Conjugates as Antinitrosating Agents: Expedient Synthesis and Remarkable Potency of 5-S-Glutathionylpiceatannol," Chem. Res. Toxicol. 21:12, pp. 2407-2413 (2008).
Tsuge et al., "Horner-Emmons Olefination of 4-Hydroxy-2-oxoalkylphosphonates and Related Compounds: Applications to the Synthesis of (±) -Gingerol, (±)-Yashabushiketol, and (±)-Dihydroyashabushiketol," Bull. Chem. Soc. Jpn. 60, 4091-4098 (1987).
Notice of Allowance and Interview Summary corresponding to U.S. Appl. No. 15/934,660 dated Feb. 21, 2019.
Bhatia et al., "Autoimmunity and Autoimmune Disease," Principles of Medical Biology, vol. 6, pp. 239-263, 244 (1996).
Brinkmann et al., "Fingolimod (FTY720): discovery and development of an oral drug to treat multiple sclerosis," Nature Reviews | Drug Discovery, vol. 9, pp. 883-897 (2010).
D'Ambrosio et al., "Chemokine receptors in inflammation: an overview," Journal of Immunological Methods, vol. 273, pp. 3-13 (2003).
Gunathilake et al., "Recent perspectives on the medicinal potential of ginger," Botanics: Targets and Therapy, vol. 5, pp. 55-63 (2015).
Hayter et al., "Updated assessment of the prevalence, spectrum and case definition of autoimmune disease," Autoimmunity Reviews, vol. 11, pp. 754-765, 756 (2012).
Judge et al., "Potassium channel blockers in multiple sclerosis: Neuronal Kv channels and effects of symptomatic treatment," Pharmacology & Therapeutics, vol. 111, pp. 224-259 (2006).
Koelink et al., "Targeting chemokine receptors in chronic inflammatory diseases: An extensive review," Pharmacology & Therapeutics, vol. 133, pp. 1-18 (2012).

(Continued)

*Primary Examiner* — Ana Z Muresan
(74) *Attorney, Agent, or Firm* — Jenkins, Wilson, Taylor & Hunt, P.A.

(57) ABSTRACT

Derivatives of 6-shogaol are described herein. Also described herein are methods of preparing the derivatives, as well as methods of using the derivatives to activate Nrf2 and to treat diseases associated with inflammation and/or oxidative stress.

19 Claims, 13 Drawing Sheets

(56) References Cited

OTHER PUBLICATIONS

Liu et al., "Identification and characterization of [6]-shogaol from ginger as inhibitor of vascular smooth muscle cell proliferation," Mol. Nutr. Food Res., vol. 59, pp. 843-852 (2015).

Office Action corresponding to U.S. Appl. No. 15/934,660 dated Sep. 27, 2018.

Rahmani et al., "Active ingredients of ginger as potential candidates in the prevention and treatment of diseases via modulation of biological activities," Int. J. Physiol. Pathophysiol. Pharmacol., vol. 6, No. 2, pp. 125-136 (2014).

Sutherland et al., "Management of Chronic Obstructive Pulmonary Disease," 350 The New England Journal of Medicine, vol. 350, pp. 2689-2697 (2004).

Zhu et al., "Synthesis, evaluation, and metabolism of novel [6]-shogaol derivatives as potent Nrf2 activators," Free Radical Biology and Medicine, vol. 95, pp. 243-254 (Jun. 2016).

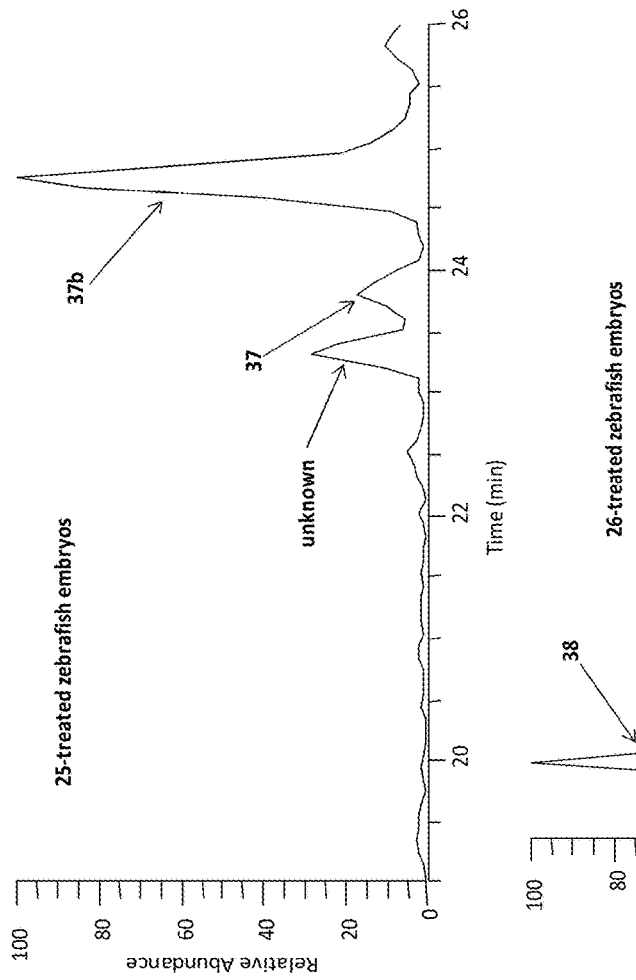
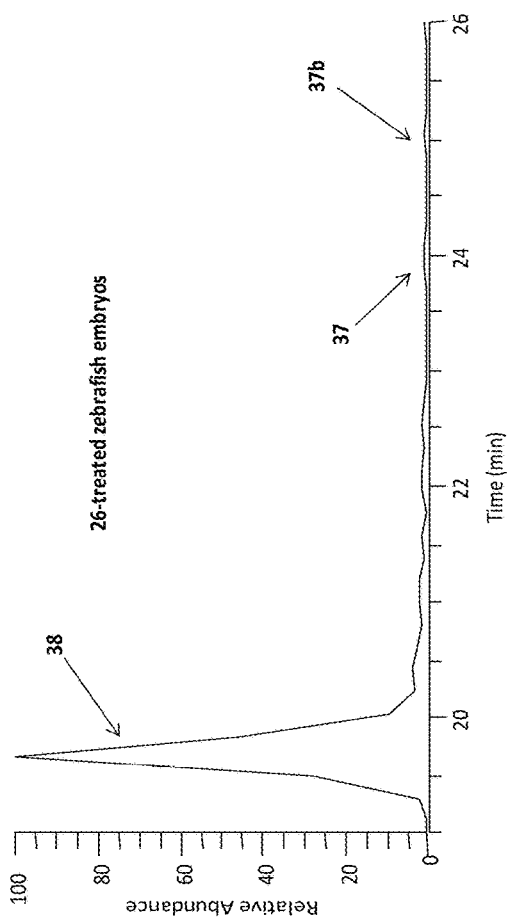
FIG. 6E
FIG. 6F

6-SHOGAOL DERIVATIVES AND ACTIVITIES THEREOF

RELATED APPLICATIONS

The presently disclosed subject matter claims the benefit of U.S. Provisional Patent Application Ser. No. 62/475,440, filed Mar. 23, 2017; the disclosure of which is incorporated herein by reference in its entirety.

PARTIES TO A JOINT RESEARCH AGREEMENT

The claimed invention was made by, on behalf of, and/or in connection with one or more of the following parties to a joint research agreement: North Carolina Agricultural and Technical State University and North Carolina Central University. The agreement was in effect on and before the date the claimed invention was made, and the claimed invention was made as a result of activities undertaken within the scope of the agreement.

TECHNICAL FIELD

The presently disclosed subject matter relates generally to 6-shogaol derivatives, to methods of preparing such, and to methods of using such derivatives.

ABBREVIATIONS percent or percentage
° C.=degrees Celsius
μl or μL=microliters
μM=micromolar
6S=[6]-shogaol
B(OMe)$_3$=trimethyl borate
Bu=butyl
CH$_3$I=methyl iodide
DCFH-DA=2',7'-dichlorodihydrofluorescindiacetate
DIPA=diisoproylamide
DMSO=dimethyl sulfoxide
Dpf=days-post-fertilization
ESI=electrospray ionization
Et=ethyl
FBS=fetal bovine serum
g=gram
GFP=green fluorescent protein
h or hr=hour
HMBC=heteronuclear multiple bond correlation
HO-1=heme oxygenase-1
IBX=2-iodoxybenzoic acid
IC$_{50}$=50% inhibitory concentration
K$_2$CO$_3$=potassium carbonate
Keap1=ketch-like ECH-associated protein 1
L=liter
LC=liquid chromatography
LDA=lithium diisopropylamide
LiHMDS=lithium bis(trimethylsilyl)amide
LiOH=lithium hydroxide
Me=methyl
MeOH=methanol
mL=milliliter
mg=milligram
min=minutes
mm=millimeters
mmol=millimole
mM=millimolar
MS=mass spectroscopy
NaHCO$_3$=sodium bicarbonate
n-BuLi=n-butyl lithium
Nrf2=nuclear factor erythroid 2-related factor 2
PBS=phosphate buffered saline
Pr=propyl
PTSA=para-toluene sulfonic acid
rt=room temperature
ROS=reactive oxygen species
SFN=sulforaphane
TFA=trifluoroacetic acid
THF=tetrahydrofuran
TMEDA=tetramethylethylenediamine

BACKGROUND

Oxidative stress is a central component of many chronic diseases. The Kelch-like ECH-associated protein 1-nuclear factor erythroid 2 like 2 ((Keap1-Nrf2) system is a major regulatory pathway of cytoprotective genes against oxidative and electrophilic stress. Activation of the Nrf2 pathway plays crucial roles in the chemopreventive effects of various inducers and small molecule Nrf2 activators, such as sulforaphane (SFN), curcumin, and chalcone derivatives have been identified as cancer chemopreventive agents.

[6]-shogaol (6S), a major component of dry ginger, was previously identified as an activator of Nrf2 in colon epithelial cells. With an α,β-unsaturated carbonyl group in the alkyl tail, 6S is a typical Michael acceptor and can activate Nrf2 via alkylation of cysteine residues of Keap1 protein. Alkylation of one or more of the cysteine residues of Keap1 by xenobiotic electrophiles appears to be one signaling mechanism for the regulation of antioxidant response element (ARE) activity through Nrf2.

However, there is an ongoing need for the identification of additional and potentially more active Nrf2 activators. There is also a need for additional compounds that could be used to treat diseases and conditions associated with oxidative stress and/or inflammation and/or that could be treated by the activation of Nrf2. Such diseases include both chronic and acute conditions, such as, for example, atherosclerosis, diabetes-related disease, and autoimmune diseases, among others.

SUMMARY

In some embodiments, the presently disclosed subject matter provides derivatives of 6-shogaol.

In some embodiments, the presently disclosed subject matter provides a compound having a structure of the formula:

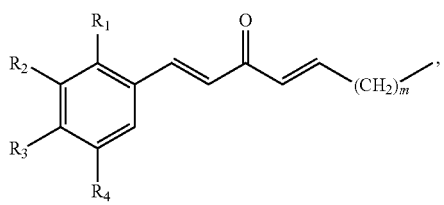

wherein: m is an integer between 0 and 4; R$_1$ is —H, halogen, halogen-substituted C$_1$-C$_4$ alkoxy, —COOH, or halogen-substituted C$_1$-C$_4$ alkyl; R$_2$ is —H, halogen, —OH, halogen-substituted C$_1$-C$_4$ alkoxy, —COOH, or halogen-substituted C$_1$-C$_4$ alkyl; and R$_3$ and R$_4$ are independently selected from the group comprising —H, —OH, amino, $C_1$-$C_4$ alkyl, $C_1$-$C_4$ alkylamino, and $C_1$-$C_4$ alkoxy, subject to the proviso that (a) when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$ and $R_1$ is —H or —F; or a pharmaceutically acceptable salt thereof.

In some embodiments, the presently disclosed subject matter provides a pharmaceutical composition comprising a compound having a structure of the formula:

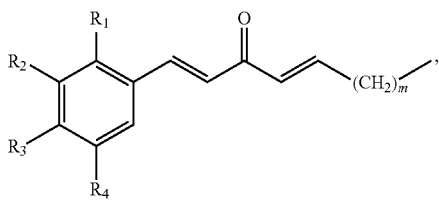

wherein: m is an integer between 0 and 4; $R_1$ is —H, halogen, halogen-substituted $C_1$-$C_4$ alkoxy, —COOH, or halogen-substituted $C_1$-$C_4$ alkyl; $R_2$ is —H, halogen, —OH, halogen-substituted $C_1$-$C_4$ alkoxy, —COOH, or halogen-substituted $C_1$-$C_4$ alkyl; and $R_3$ and $R_4$ are independently selected from the group comprising —H, —OH, amino, $C_1$-$C_4$ alkyl, $C_1$-$C_4$ alkylamino, and $C_1$-$C_4$ alkoxy, subject to the proviso that (a) when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$ and $R_1$ is —H or —F; or a pharmaceutically acceptable salt thereof; and a pharmaceutically acceptable carrier.

In some embodiments, the presently disclosed subject matter provides a compound having a structure of one of the formulas:

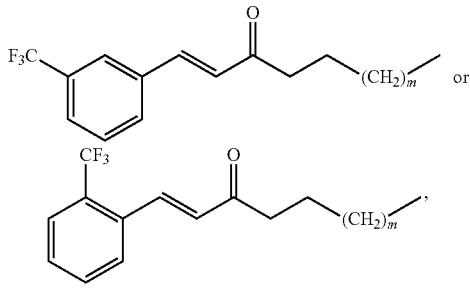

wherein: m is 0 to 4; or a pharmaceutically acceptable salt thereof.

In some embodiments, the presently disclosed subject matter provides a pharmaceutical composition comprising a compound having a structure of one of the formulas:

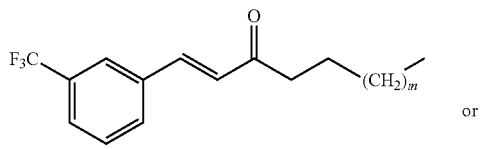

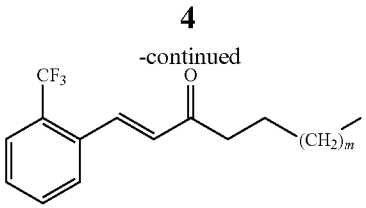

wherein: m is 0 to 4; or a pharmaceutically acceptable salt thereof; and a pharmaceutically acceptable carrier.

It is an object of the presently disclosed subject matter to provide 6-shogaol derivatives and pharmaceutical compositions thereof.

An object of the presently disclosed subject matter having been stated hereinabove, and which is achieved in whole or in part by the presently disclosed subject matter, other objects will become evident as the description proceeds when taken in connection with the accompanying drawings as best described herein.

BRIEF DESCRIPTION OF THE DRAWINGS

FIG. 6E is a graph showing an extracted ion chromatogram of compound 25-treated zebrafish embryos obtained by positive electrospray ionization mass spectrometry (ESI/MS) interface.

FIG. 6F is a graph showing an extracted ion chromatogram of compound 26-treated zebrafish embryos obtained by positive electrospray ionization mass spectrometry (ESI/MS) interface.

DETAILED DESCRIPTION

Figure 1:
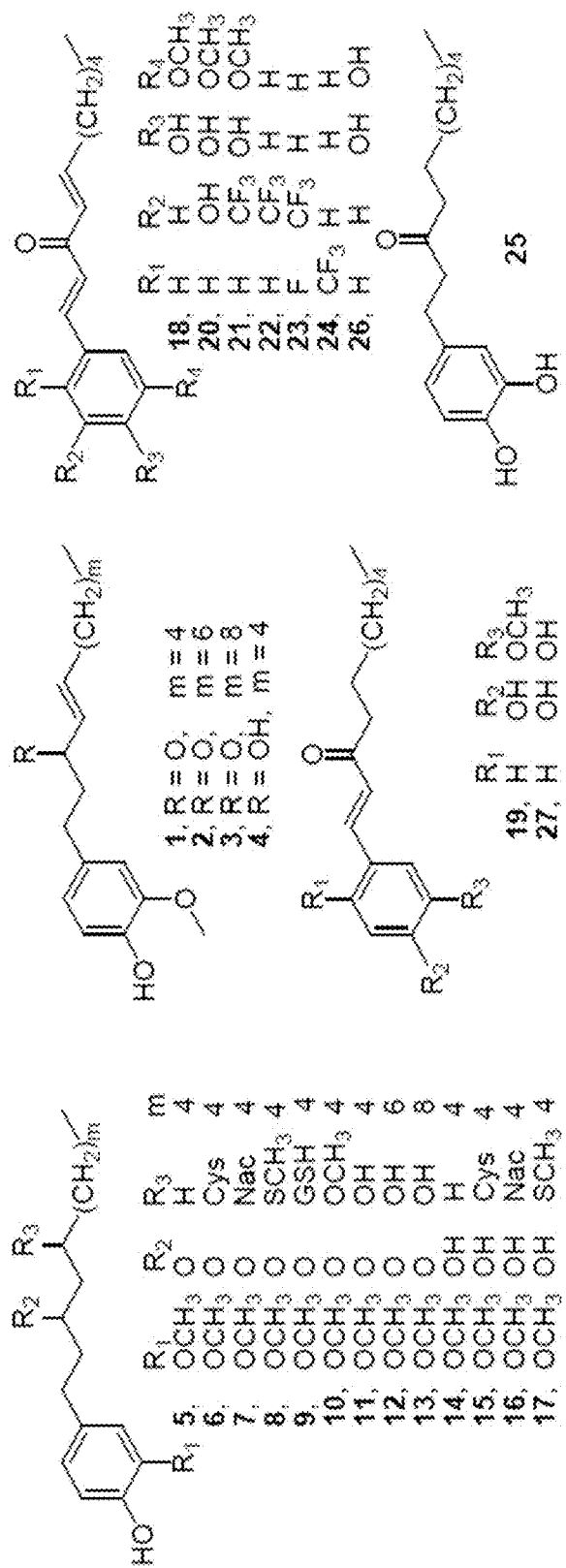
FIG. 1 is a schematic diagram showing the chemical structures of compounds 1-27.

The presently disclosed subject matter will now be described more fully. The presently disclosed subject matter can, however, be embodied in different forms and should not be construed as limited to the embodiments set forth herein below and in the accompanying Examples. Rather, these embodiments are provided so that this disclosure will be thorough and complete, and will fully convey the scope of the embodiments to those skilled in the art.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a", "an", and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or."

As used herein "another" can mean at least a second or more.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed subject matter can include the use of either of the other two terms.

Unless otherwise indicated, all numbers expressing quantities of weight, mass, volume, time, activity, percentage (%), and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value is meant to encompass variations of in one example ±20% or ±10%, in another example ±5%, in another example ±1%, and in still another example ±0.1% from the specified amount, as such variations are appropriate to perform the disclosed methods.

The terms "halo" and "halogen" refer to —F, —Cl, —Br, or —I.

The term "carbonyl" refers to a group having the structure —C(=O)—.

As used herein, an "unsaturated carbonyl" refers to the general structures:

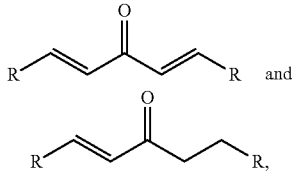

wherein each R is H, alkyl, substituted alkyl, aralkyl, substituted aralkyl, aryl or substituted aryl. In these compounds, the carbonyl group is conjugated with one or two alkenes, from which they derive special properties.

"Conjugated" as used with regard to the conjugation of the carbonyl with alkenes or the conjugation of particular functional groups with other functional groups can refer to structures wherein p-orbitals can overlap with each other over intervening sigma ($\sigma$) bonds. Thus, a "conjugated" system can include alternating single and double bonds and/or an aromatic moiety connected via a single bond to a double bond. Generally the unsaturated carbonyl groups in the compounds of the present application are found in an alkyl side chain. The term "enone" can also be used to refer to the group —C(=O)—CR=CR—R.

As used herein, a "catechol moiety" refers to a 6-membered aromatic ring having three or more substituents, wherein two substituents are —OR groups at C-3 and C-4 ring positions, wherein R is hydrogen or an alkyl group. Generally the third substituent at the C-1 ring position is an aliphatic chain containing an unsaturated carbonyl.

As used herein, "alkyl" refers to a straight or branched saturated hydrocarbon chain. The term "$C_1$-$C_4$ alkyl" refers to straight or branched alkyl groups comprising between 1 and 4 carbons, i.e., methyl (—$CH_3$ or -Me); ethyl (—$CH_2CH_3$ or -Et); propyl (—Pr), including n-propyl (—$CH_2CH_2CH_3$ or —"Pr) and isopropyl (—$CH(CH_3)_2$ or —$^iPr$); and butyl (—Bu), including n-butyl (—$(CH_2)_3CH_3$ or —"Bu), sec-butyl (—$CH(CH_3)CH_2CH_3$ or —$^sBu$), tert-butyl (—$C(CH_3)_3$ or —$^tBu$) and iso-butyl (—$CHCH(CH_3)_2$ or —$^iBu$).

As used herein, "alkenyl" refers to a straight or branched hydrocarbon chain comprising one or more carbon-carbon double bonds.

The term "aralkyl" as used herein refers to a -alkyl-aryl group, e.g., benzyl, phenylethyl, and naphthylmethyl.

The term "aryl" as used herein refers to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds (e.g., wherein one or more carbon atoms in an aromatic ring is replaced by oxygen, sulfur or nitrogen). The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The terms "hydroxyl" and "hydroxyl" as used herein refer to the —OH group. In some embodiments, a hydroxyl group can be directly attached to an aromatic group, e.g., a phenyl group, and can also be referred to as a "phenol."

The terms "alkoxy" and "alkoxyl" as used herein refer to the group —OR, wherein R is alkyl. In some embodiments, the term alkoxy refers to $C_1$-$C_4$ alkoxy groups, i.e., alkoxy groups where R is methyl, ethyl, propyl, or butyl. Thus, $C_1$-$C_4$ alkoxy includes methoxy (—$OCH_3$ or —OMe), ethoxy (—$OCH_2CH_3$ or —OEt), isopropoxy (—OCH($CH_3$)$_2$ or —$O^iPr$), n-propoxy (—$O(CH_2)_2CH_3$ or —$O^nPr$), n-butoxy (—$O(CH_2)_3CH_3$ or —$O^nBu$), sec-butoxy (—OCH($CH_3$)$CH_2CH_3$ or —$O^sBu$), tert-butoxy (—$OC(CH_3)_3$ or —$O^tBu$), and iso-butoxy (—$OCH_2CH(CH_3)_2$ or —$O^iBu$).

The terms "carboxy", "carboxyl", "carboxylate" and "carboxylic acid" as used herein refer to the group —C(═O)OH (also depicted as —COOH) and the deprotonated form thereof (i.e., C(═O)O$^-$).

The term "amino" as used herein refers to the group —$NH_2$.

The term "alkylamino" as used herein refers to the group —$NR_2$, wherein each R is selected from the group comprising H and alkyl and wherein at least one R is alkyl. Thus, "alkylamino" as used herein refers to —N(H)(alkyl) (i.e., monoalkylamino) and —N(alkyl)$_2$ (dialkylamino). In some embodiments "alkylamino" refers to $C_1$-$C_4$ alkylamino, wherein each alkyl group in the alkylamino moiety is selected from a $C_1$-$C_4$ straight or branched alkyl group.

The term "halogen-substituted $C_1$-$C_4$ alkoxy" as used herein refers to a $C_1$-$C_4$ alkoxy group wherein one or more hydrogen atoms are replaced by a halogen (e.g., —F). In some embodiments, "halogen-substituted $C_1$-$C_4$ alkoxy" refers to a halogen-substituted methoxy group (e.g., a tri- or dihalogen-substituted methoxy group (e.g., —$OCF_3$ or —$OCHF_2$)).

The term "halogen-substituted $C_1$-$C_4$ alkyl" refers herein to a $C_1$-$C_4$ alkyl group wherein one or more hydrogen atoms are replaced by a halogen (e.g., —F). In some embodiments, the halogen-substituted $C_1$-$C_4$ alkyl group is a methyl group substituted with one, two or three halogen groups. In some embodiments, the group is a trihalosubstituted methyl group (e.g., —$CF_3$).

When the term "independently selected" is used, the substituents being referred to (e.g., R groups, such as groups $R_1$ and $R_2$) can be identical or different. For example, both $R_1$ and $R_2$ can be substituted alkyls, or $R_1$ can be hydrogen and $R_2$ can be alkyl and the like.

As used herein, "pharmaceutically acceptable" means that the material is suitable for administration to a subject (e.g., a human subject) and will allow desired treatment to be carried out without giving rise to unduly deleterious adverse effects. The severity of the disease and the necessity of the treatment are generally taken into account when determining whether any particular side effect is unduly deleterious.

As used herein, the term "therapeutically effective" refers to provision of some improvement or benefit to the subject. Alternatively stated, a "therapeutically effective amount" is an amount that will provide some alleviation, mitigation, or decrease in at least one clinical symptom in the subject. Those skilled in the art will appreciate that the therapeutic effects need not be complete or curative, as long as some benefit is provided to the subject. The therapeutically useful response can provide some alleviation, mitigation, or decrease in at least one clinical symptom in the subject. The terms also include an amount that will prevent or delay at least one clinical symptom in the subject and/or reduce and/or delay the severity of the onset of a clinical symptom in a subject relative to what would occur in the absence of the methods of the presently disclosed subject matter. Those skilled in the art will appreciate that the therapeutically useful response need not be complete or curative or prevent permanently, as long as some benefit is provided to the subject.

As used herein, the terms "treatment," "treat," and "treating" refer to reversing, alleviating, delaying the onset of, inhibiting the progress of or preventing a disease or disorder. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example, to prevent or delay their recurrence.

As used herein, the term "treatment effective amount" (and grammatical variants thereof) refers to an amount that is sufficient to provide some improvement or benefit to the subject. Alternatively stated, a "treatment effective amount" is an amount that will provide some alleviation, mitigation, decrease, or stabilization in at least one clinical symptom in the subject. Those skilled in the art will appreciate that the therapeutic effects need not be complete or curative, as long as some benefit is provided to the subject.

Many serious diseases involve inflammatory processes, including diseases not typically attributed to inflammation, such as: atherosclerosis, in which activated macrophages contribute to the formation and rupture of atherosclerotic plaques; and diabetes, particularly as tied to the development of insulin resistance.

Thus, a variety of diseases are associated, directly or indirectly, with oxidative stress and inflammation, including but not limited to autoimmune diseases, such as rheumatoid arthritis, lupus, psoriasis, and multiple sclerosis; neurodegenerative diseases, such as Alzheimer's and Parkinson's; chronic organ failure, such as renal failure, heart failure, liver failure, and chronic obstructive pulmonary disease; atherosclerosis, systemic cardiovascular disease and chronic kidney disease, as well as acute disorders, including acute failure of the pancreas, kidneys, liver, lungs, or heart. Additionally, disorders have been identified as associated, directly or indirectly, with oxidative stress and inflammation, including inflammatory bowel disease; transplant failure and rejection; degenerative conditions such as osteoarthritis and osteoporosis; cystic fibrosis; seizure disorders, and diabetes, diabetes-related complications and diseases (e.g. hyperglycemia induced changes such as retinopathy, neuropathy, nephropathy, cardiomyopathy, as well as pancreatic damage).

In some embodiments, the presently disclosed compounds can contain one or more chiral centers and/or double bonds and therefore, can exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The presently disclosed compounds can also exist in several tautomeric forms including the enol form, the keto form and mixtures thereof. Accordingly, the chemical structures depicted herein encompass all possible tautomeric forms of the illustrated compounds. The presently disclosed compounds also include isotopically labeled compounds where one or more atoms have an atomic mass different from the atomic mass conventionally found in nature. Examples of isotopes that can be incorporated into the presently disclosed compounds include, but are not limited to, $^2H$, $^3H$, $^{13}C$, $^{14}C$, $^{15}N$, $^{18}O$, $^{17}O$, and $^{18}F$.

A composition comprising one or more of the presently disclosed compounds, or a pharmaceutically acceptable salt or salts thereof, include but are not limited to acid addition and/or base salts. Pharmaceutically acceptable salts of the compounds can include the acid addition and base salts (including disalts) thereof, such as L-tartrate salt. Examples of suitable salts can be found for example in Stahl and Wermuth, *Handbook of Pharmaceutical Salts Properties, Selection, and Use*, Wiley-VCH, Weinheim, Germany (2002); and Berge et al., "Pharmaceutical Salts," *J. of Pharmaceutical Science*, 1977; 66:1-19.

Acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present application.

Pharmaceutically acceptable base addition salts can be formed with metals or amines, such as alkali and alkaline earth metal hydroxides, or of organic amines. Examples of metals used as cations include, but are not limited to, aluminum, calcium, magnesium, potassium, sodium, and the like. Examples of suitable amines include, but are not limited to, arginine, choline, chloroprocaine, N,N'-dibenzylethylenediamine, diethylamine, diethanolamine, diolamine, ethylenediamine (ethane-1,2-diamine), glycine, lysine, meglumine, N-methylglucamine, olamine, procaine (benzathine), and tromethamine.

The base addition salts of acidic compounds can be prepared by contacting the free acid form with a sufficient amount of the desired base to produce the salt in the conventional manner. The free acid form can be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present application.

As used herein, the phrase "nutraceutical composition" or variants thereof refers to compositions containing a compound disclosed herein and further containing a food or a liquid, part of a food or a liquid, or is an addition to a food or a liquid, wherein such composition provides medical or health benefits, including the prevention and treatment of disease either alone or in combination with a primary therapy, or the trigger of a beneficial physiological response.

A nutraceutical composition as disclosed herein provides a nutritional source, thus, a nutraceutical composition can be a food product, foodstuff, functional food, or a supplement composition for a food product or a foodstuff. As used herein, the term food product refers to any food which provides a nutritional source and is suitable for oral consumption by humans or animals. The food product can be a prepared and packaged food or an animal feed. As used herein, the term foodstuff refers to a nutritional source for human or animal consumption. Functional foods are foods consumed as part of a diet which are demonstrated to have physiological benefits beyond basic nutritional functions. Food products, foodstuffs, or functional foods include but are not limited to beverages, such as non-alcoholic and alcoholic drinks as well as liquid preparations to be added to drinking water and liquid food, and solid or semi-solid foods. Non-alcoholic drinks include but are not limited to nutritional shakes, soft drinks; sport drinks; fruit juices; and milk and other dairy drinks such as yogurt drinks and protein shakes. Examples of solid or semi-solid food include, but are not limited to, baked goods; puddings; dairy products; confections; snack foods; or frozen confections or novelties; prepared frozen meals; candy; liquid food such as soups; spreads; sauces; salad dressings; prepared meat products; cheese; yogurt and any other fat or oil containing foods; and food ingredients.

The presently disclosed compounds and their pharmaceutically acceptable salts can be administered by a variety of approaches, including orally, parenterally, by inhalation spray, topically, or rectally in formulations containing pharmaceutically acceptable carriers, e.g., for use in intravenous or sub-cutaneous administration. The term "carrier" as used herein can be used herein interchangeable with "excipient" and/or "vehicle." The compounds can also be administered as depot formulations. Pharmaceutical compositions containing the active ingredient can be in any form suitable for the intended method of administration.

Generally, the compounds of the presently disclosed subject matter (or their pharmaceutically acceptable salts) can be provided in a composition further comprising a pharmaceutically acceptable carrier, e.g., a carrier that is pharmaceutically acceptable for use in humans. In some embodiments, the carrier or excipient is acceptable for use in animals (e.g., in veterinary settings). In some embodiments, the pharmaceutically acceptable carrier can be a liquid, such as water, saline, glycerol and/or ethanol. Additionally, auxiliary substances, such as wetting or emulsifying agents or pH buffering substances, can be present in such compositions.

The term "parenteral" as used herein includes subcutaneous, intravenous, intramuscular, and intraarterial injections with a variety of infusion techniques. Intraarterial and intravenous injection as used herein includes administration through catheters.

In some embodiments, the subject treated according to the presently disclosed subject matter is a human subject, although it is to be understood that the methods described herein are effective with respect to all vertebrate species, which are intended to be included in the term "subject."

More particularly, provided herein is the treatment of mammals and birds, such as humans, as well as those mammals and birds of importance due to being endangered (such as Siberian tigers), of economical importance (animals raised on farms for consumption by humans) and/or social importance (animals kept as pets or in zoos) to humans, for instance, carnivores other than humans (such as cats and dogs), rodents (such as mice, rats, hamsters, gerbils, guinea pigs, porcupine, prairie dogs, squirrels, beaver), rabbits, swine (pigs, hogs, and wild boars), ruminants (such as cattle, oxen, sheep, giraffes, deer, goats, bison, and camels), horses, poultry (e.g., chickens, ducks, geese, and turkeys) and parrots. Thus, embodiments of the methods described herein include the treatment of livestock, including, but not limited to, domesticated swine (pigs and hogs), ruminants, horses, poultry, and the like.

In some embodiments, the subject is a subject who has been diagnosed with a cancer. The cancer can be selected from the group including, but not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, non-secretory myeloma, osteosclerotic myeloma, plasma cell leukemia, solitary plasmacytoma and extramedullary plasmacytoma; Waldenström's acroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, non-glial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but not limited to Cushing's disease, prolactin-secreting tumor, acromegaly, and diabetes insipidus; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; head and neck cancers, such as but not limited to head and neck squamous cell cancers (HNSCCs), esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. In some embodiments, the subject has colon cancer.

In some embodiments, the subject is a subject who has been diagnosed with a disease or condition associated with oxidative stress and/or inflammation, such as, but not limited to, atherosclerosis, an autoimmune disease (e.g., rheumatoid arthritis, lupus, psoriasis, and multiple sclerosis), a neurodegenerative disease (e.g., Alzheimer's or Parkinson's disease), organ failure (e.g., kidney failure, heart failure, liver failure), systemic cardiovascular disease, chronic kidney disease, acute failure of the pancreas, kidneys, liver, lungs or heart, inflammatory bowel disease transplant failure/rejection, a degenerative disease (e.g., osteoarthritis, osteoporosis, etc.), cystic fibrosis, a seizure disorder, diabetes, and diabetes-related complications and diseases (e.g. hyperglycemia induced changes such as retinopathy, neuropathy, nephropathy, cardiomyopathy, as well as pancreatic damage).

It will be understood that the specific dose level for any particular subject will depend on a variety of factors including the activity of the specific compound employed; the age, body weight, general health, sex and diet of the individual being treated; the time and route of administration; the rate of excretion; other drugs which have previously been administered, as is well understood by those skilled in the art. Convenient dosing includes, but is not limited to, a once a day or twice a day administration, such as a tablet or capsule, as well as intravenous infusions. The use of time-release preparations to control the rate of release of the active ingredient as well as continuous infusions can also be employed. The dose can be administered in as many divided doses as is convenient.

Unit dosage formulations can be those containing a daily dose or unit, daily sub-dose, or an appropriate fraction thereof, of a compound of the present application or a pharmaceutically acceptable salt thereof. The unit dose can be for oral consumption, such as by a tablet or capsule, or for infusion, or administered by other means as disclosed herein. The amount can be provided by oral consumption, infusion, or administered by other means familiar to those of skill in the art, such as transdermal or transmucosal.

In other embodiments, the unit dose can be provided as an infusion. For example, the compositions described herein can be administered intravenously, such as by an IV drip using IV solutions well known in the art (e.g., isotonic saline (0.9% NaCl) or dextrose solution (e.g., 5% dextrose), optionally the intravenous solution further includes preservatives, e.g. sodium metabisulfite.

In some embodiments, the presently disclosed subject matter provides a compound comprising a substituted phenyl group (e.g., a catechol) conjugated to a carbonyl (e.g., an unsaturated carbonyl). In some embodiments, the presently disclosed subject matter provides a compound having a structure of the formula:

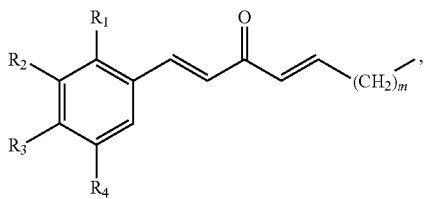

wherein: m is an integer between 0 and 4 (i.e., 1, 2, 3, or 4); $R_1$ is —H, halogen, halogen-substituted $C_1$-$C_4$ alkoxy (e.g., —$OCF_3$ and —$OCHF_2$), —COOH, or halogen-substituted $C_1$-$C_4$ alkyl (e.g., —$CF_3$); $R_2$ is —H, halogen, —OH, halogen-substituted $C_1$-$C_4$ alkoxy, —COOH, or halogen-substituted $C_1$-$C_4$ alkyl; and $R_3$ and $R_4$ are independently selected from the group comprising —H, —OH, amino, $C_1$-$C_4$ alkyl, $C_1$-$C_4$ alkylamino, and $C_1$-$C_4$ alkoxy, subject to the proviso that (a) when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$ and $R_1$ is —H or —F; or a pharmaceutically acceptable salt thereof.

In some embodiments, $R_1$ and/or $R_2$ is halogen and the halogen is —F, —Cl, or —Br. In some embodiments, the halogen is —F or —Cl. In some embodiments, the halogen is —F. In some embodiments, $R_1$ and/or $R_2$ is a halogen-substituted methoxy or methyl group. In some embodiments, $R_1$ and/or $R_2$ is —$CF_3$, —$OCF_3$, or —$OCHF_2$. In some embodiments, $R_1$ is —H, —F, —$OCF_3$, —$OCHF_2$, —COOH or —$CF_3$; and $R_2$ is —H, —F, —OH, —$OCF_3$, —$OCHF_2$, —COOH or —$CF_3$. In some embodiments, $R_1$ is —H, —F, or —$CF_3$. In some embodiments, $R_1$ is —H or —$CF_3$. In some embodiments, $R_2$ is —H, —F, —OH, or —$CF_3$. In some embodiments, $R_2$ is —F, —OH, or —$CF_3$. In some embodiments, $R_2$ is —F or —$CF_3$.

In some embodiments, $R_3$ and/or $R_4$ are selected from —H, —OH, $C_1$-$C_4$ alkyl, and $C_1$-$C_4$ alkoxy or $R_3$ and/or $R_4$ are selected from —H, —OH, and $C_1$-$C_4$ alkoxy, subject to the proviso that (a) when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$ and $R_1$ is —H or —F; or a pharmaceutically acceptable salt thereof. In some embodiments, $R_3$ and/or $R_4$ are selected from —OH and $C_1$-$C_4$ alkoxy subject to the proviso that (a) when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$ and $R_1$ is —H or —F; or a pharmaceutically acceptable salt thereof.

In one variation of any disclosed embodiment or aspect, m is 0, 2 or 4; in another variation, m is 4.

In some embodiments, $R_1$ is —H, —F, —$OCF_3$, —$OCHF_2$, —COOH or —$CF_3$; and $R_2$ is —H, —F, —OH, —$OCF_3$, —$OCHF_2$, —COOH or —$CF_3$. In another embodiment, $R_1$ is —H; $R_2$ is selected from —H, —F, —OH, and —$CF_3$; and $R_3$ and $R_4$ are independently selected from the group comprising —OH and $C_1$-$C_4$ alkoxy, subject to the proviso that when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy. Alternately, $R_1$ is —H; $R_2$ is selected from —F, —OH, and —$CF_3$; and $R_3$ and $R_4$ are independently selected from the group comprising —OH and $C_1$-$C_4$ alkoxy. In another variation, $R_3$ and $R_4$ are independently $C_1$-$C_4$ alkoxy. In another variation, $R_2$ is —F or —$CF_3$. In another embodiment, $R_2$ is —F, —OH, or $CF_3$; and $R_3$ and $R_4$ are independently selected from —OH and $C_1$-$C_4$ alkoxy. In yet another embodiment $R_2$ is —F or $CF_3$; and $R_3$ and $R_4$ are independently selected from —OH, methoxy, isopropoxy, and tert-butoxy. In yet another embodiment, $R_2$ is —F.

In one embodiment, the compound is selected from the group comprising:

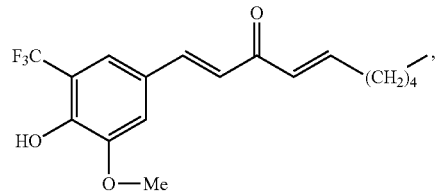

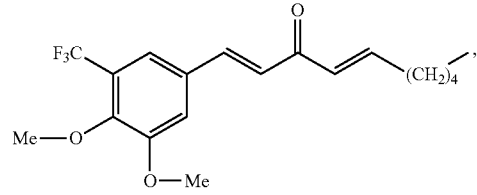

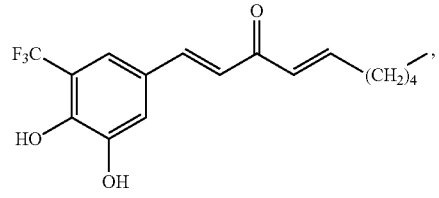

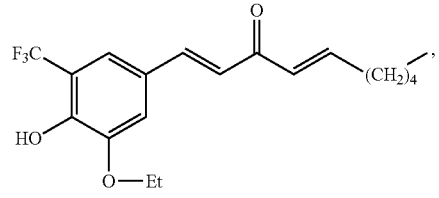

-continued

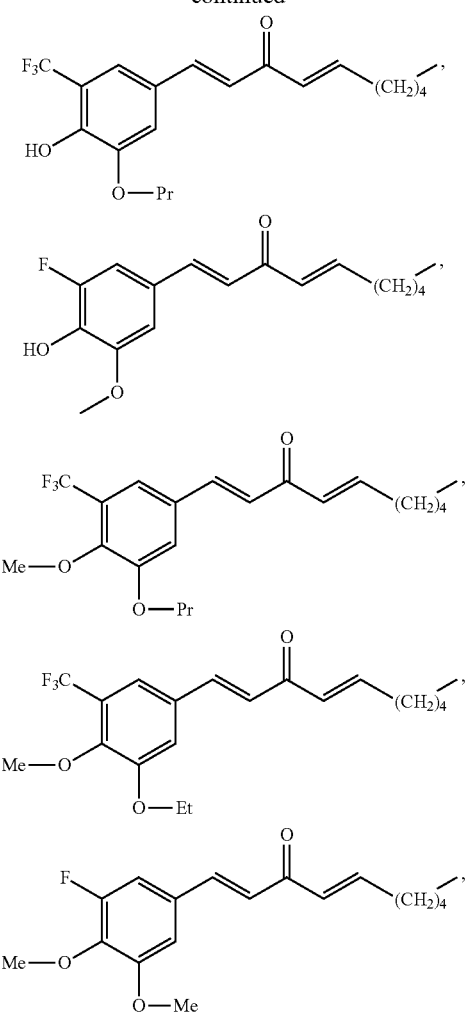

and pharmaceutically acceptable salts thereof.

Alternately, the compound is selected from the group comprising:

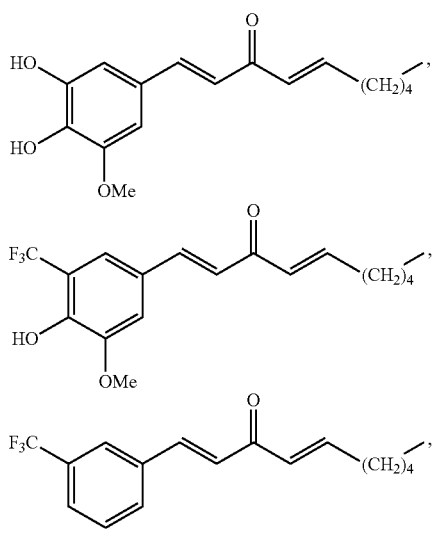

-continued

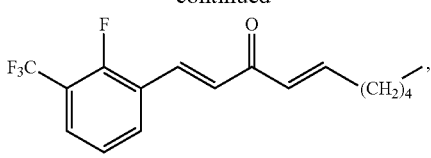

and pharmaceutically acceptable salts thereof.

In one embodiment, $R_1$ is —H; $R_2$ is —CF$_3$; $R_3$ is —OH; and $R_4$ is methoxy; and the compound has the formula:

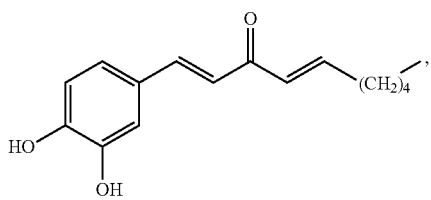

wherein m is 0, 2, or 4. Alternately, m is 4.

In one aspect, the presently disclosed subject matter provides a compound having a structure of one of the formulas:

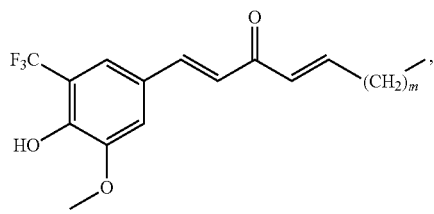

or

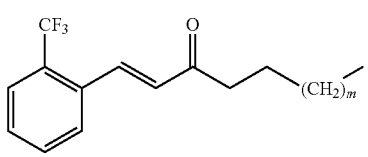

wherein: m is 0 to 4; or a pharmaceutically acceptable salt thereof. Alternately, m is 0, 2, or 4; in still another alternative, m is 4.

In some embodiments, the presently disclosed subject matter provides a pharmaceutical composition comprising one or more compound comprising a substituted phenyl group conjugated to a carbonyl and a pharmaceutically acceptable carrier. In some embodiments, the presently disclosed subject matter provides a pharmaceutical composition comprising a compound having a structure of the formula:

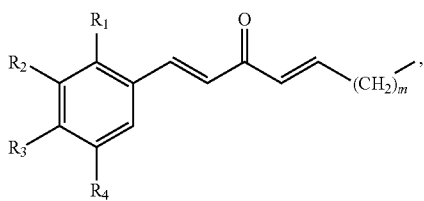

wherein: m is an integer between 0 and 4; $R_1$ is —H, halogen, halogen-substituted $C_1$-$C_4$ alkoxy, —COOH, or halogen-substituted $C_1$-$C_4$ alkyl; $R_2$ is —H, halogen, —OH, halogen-substituted $C_1$-$C_4$ alkoxy, —COOH, or halogen-substituted $C_1$-$C_4$ alkyl; and $R_3$ and $R_4$ are independently selected from the group comprising —H, —OH, amino, $C_1$-$C_4$ alkyl, $C_1$-$C_4$ alkylamino, and $C_1$-$C_4$ alkoxy, subject to the proviso that (a) when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$ and $R_1$ is —H or —F; or a pharmaceutically acceptable salt thereof; and a pharmaceutically acceptable carrier.

In some embodiments, $R_1$ and/or $R_2$ is halogen and the halogen is —F, —Cl, or —Br. In some embodiments, the halogen is —F or —Cl. In some embodiments, the halogen is —F. In some embodiments, $R_1$ and/or $R_2$ is a halogen-substituted methoxy or methyl group. In some embodiments, $R_1$ and/or $R_2$ is —$CF_3$, —$OCF_3$, or —$OCHF_2$. In some embodiments, $R_1$ is —H, —F, —$OCF_3$, —$OCHF_2$, —COOH or —$CF_3$; and $R_2$ is —H, —F, —OH, —$OCF_3$, —$OCHF_2$, —COOH or —$CF_3$. In some embodiments, $R_1$ is —H, —F, or —$CF_3$. In some embodiments, $R_1$ is —H or —$CF_3$. In some embodiments, $R_2$ is —H, —F, —OH, or —$CF_3$. In some embodiments, $R_2$ is —F, —OH, or —$CF_3$. In some embodiments, $R_2$ is —F or —$CF_3$.

In some embodiments, $R_3$ and/or $R_4$ are selected from —H, —OH, $C_1$-$C_4$ alkyl, and $C_1$-$C_4$ alkoxy or $R_3$ and/or $R_4$ are selected from —H, —OH, and $C_1$-$C_4$ alkoxy, subject to the proviso that (a) when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$ and $R_1$ is —H or —F; or a pharmaceutically acceptable salt thereof. In some embodiments, $R_3$ and/or $R_4$ are selected from —OH, and $C_1$-$C_4$ alkoxy, subject to the proviso that (a) when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$ and $R_1$ is —H or —F; or a pharmaceutically acceptable salt thereof.

In one variation of any disclosed embodiment or aspect, m is 0, 2 or 4; in another variation, m is 4.

In some embodiments, $R_1$ is —H, —F, —$OCF_3$, —$OCHF_2$, —COOH or —$CF_3$; and $R_2$ is —H, —F, —OH, —$OCF_3$, —$OCHF_2$, —COOH or —$CF_3$. In another embodiment, $R_1$ is —H; $R_2$ is selected from —H, —F, —OH, and —$CF_3$; and $R_3$ and $R_4$ are independently selected from the group comprising —OH and $C_1$-$C_4$ alkoxy, subject to the proviso that when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy. Alternately, $R_1$ is —H; $R_2$ is selected from —F, —OH, and —$CF_3$; and $R_3$ and $R_4$ are independently selected from the group comprising —OH and $C_1$-$C_4$ alkoxy. In another variation, $R_3$ and $R_4$ are independently $C_1$-$C_4$ alkoxy. In another variation, $R_2$ is —F or —$CF_3$. In another embodiment, $R_2$ is —F, —OH, or $CF_3$; and $R_3$ and $R_4$ are independently selected from —OH and $C_1$-$C_4$ alkoxy. In yet another embodiment $R_2$ is —F or $CF_3$; and $R_3$ and $R_4$ are independently selected from —OH, methoxy, isopropoxy, and tert-butoxy. In yet another embodiment, $R_2$ is —F.

In some embodiments, the pharmaceutical composition comprises a compound selected from the group comprising:

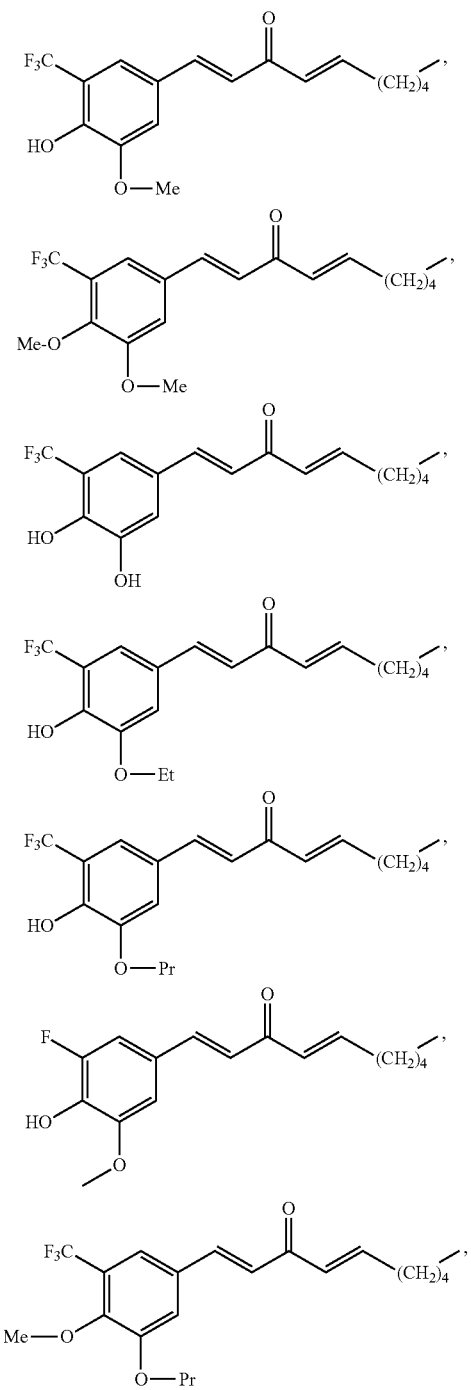

-continued

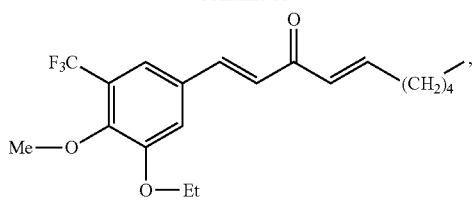

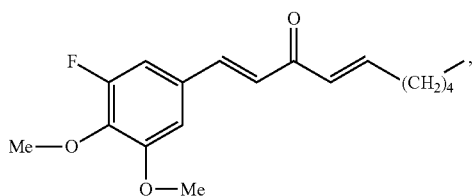

and pharmaceutically acceptable salts thereof.

Alternately, in some embodiments, the pharmaceutical composition comprises a compound selected from the group comprising:

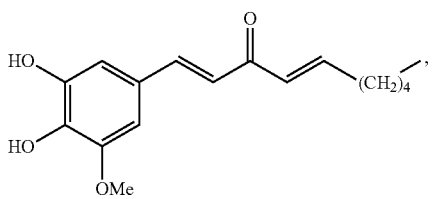

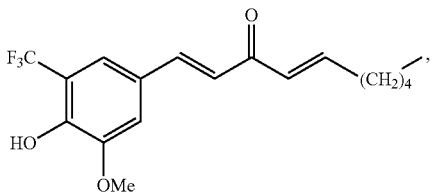

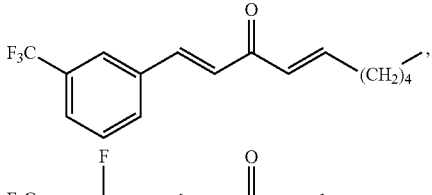

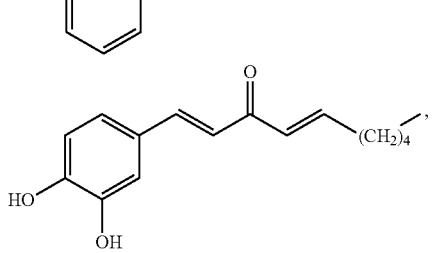

and pharmaceutically acceptable salts thereof.

In one embodiment, $R_1$ is —H; $R_2$ is —CF$_3$; $R_3$ is —OH; and $R_4$ is methoxy; and the pharmaceutical composition comprises a compound that has a structure of the formula:

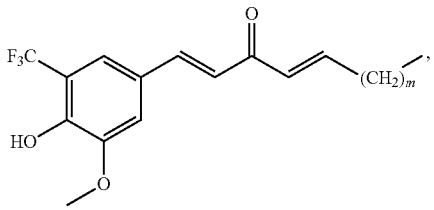

wherein m is 0, 2, or 4. Alternately, m is 4.

In some embodiments, the presently disclosed subject matter provides a pharmaceutical composition comprising a compound having a structure of one of the formulas:

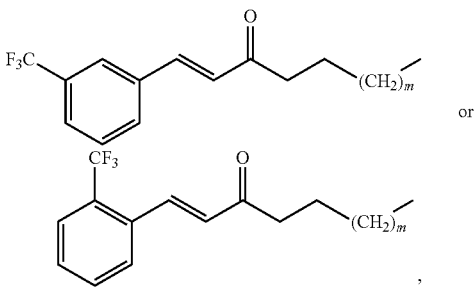

wherein: m is 0 to 4; or a pharmaceutically acceptable salt thereof; and a pharmaceutically acceptable carrier. In some embodiments, m is 0, 2, or 4. In some embodiments, m is 4.

In some embodiments, the present application provides a kit for treating cancer in a subject, the kit comprising a compound of the present application or the pharmaceutical composition of the present application, and instructions for using the kit. In some embodiments, the subject is an animal, such as a human.

In other embodiments, the present application provides a kit for treating a disease associated with inflammation and/or oxidative stress in a subject in need thereof, wherein the disease is treatable by activation of Nrf2, the kit comprising a compound of the present application or the pharmaceutical composition of the present application, and instructions for using the kit. In some embodiments, the subject is an animal, such as a human.

In one aspect, the presently disclosed subject matter provides a method of preparing a compound having a structure of the formula:

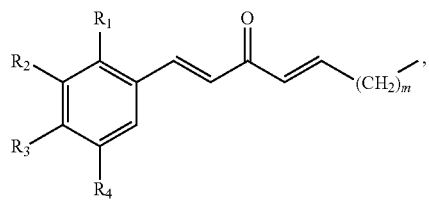

wherein: m is an integer between 0 and 4; $R_1$ is —H, -halogen, halogen-substituted $C_1$-$C_4$ alkoxy, halogen-substituted $C_1$-$C_4$ alkyl, or —COOH; $R_2$ is —H, -halogen, —OH, halogen-substituted $C_1$-$C_4$ alkoxy, halogen-substituted $C_1$-$C_4$ alkyl, or —COOH; and $R_3$ and $R_4$ are independently selected from the group comprising —H, —OH, amino, $C_1$-$C_4$ alkyl, $C_1$-$C_4$ alkylamino, and $C_1$-$C_4$ alkoxy, subject to the proviso that (a) when $R_1$ and $R_2$ are each —H, $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is —OH or $C_1$-$C_4$ alkoxy; and (b) when $R_4$ is —H, $R_3$ is —H, $R_2$ is —$CF_3$ and $R_1$ is —H or —F; wherein the method comprises performing a mixed aldol condensation between an aromatic aldehyde and a methyl ketone and, if necessary, dehydrating a resulting alcohol intermediate.

In some embodiments, the wherein the method comprises: (a) providing an aromatic aldehyde having the structure:

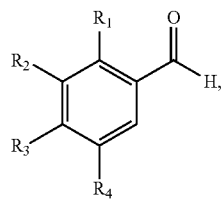

wherein $R_1$ is —H, -halogen, halogen-substituted $C_1$-$C_4$ alkoxy, halogen-substituted $C_1$-$C_4$ alkyl, —COOH, or protected —COOH; $R_2$ is —H, -halogen, —OH, protected —OH, halogen-substituted $C_1$-$C_4$ alkoxy, halogen-substituted $C_1$-$C_4$ alkyl, —COOH, or protected —COOH; and $R_3$ and $R_4$ are independently selected from the group comprising —H, —OH, protected —OH, amino, protected amino, $C_1$-$C_4$ alkylamino, and $C_1$-$C_4$ alkoxy; (b) contacting the aromatic aldehyde with an enolate formed by reacting a base, such as an alkyl lithium (e.g., n-butyl lithium (n-BuLi), LDA (lithium diisopropylamide), LiHMDS (lithium bis(trimethylsilyl)amide), or NaH, with a methyl ketone having a structure of the formula:

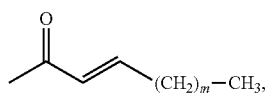

wherein m is an integer between 0 and 4, thereby providing an alcohol having a structure of the formula:

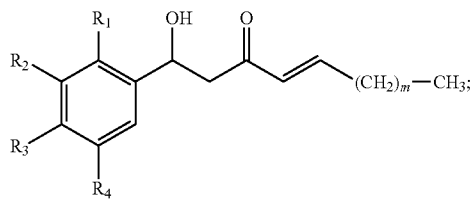

and (c) contacting the alcohol formed in step (b) with an suitable acid (e.g., PTSA) to dehydrate the alcohol to form a double bond (i.e., between the aromatic ring and the ketone moiety), thereby providing a conjugated ketone; optionally wherein the method further comprises removing a protecting group from one or more of $R_1$-$R_4$. For example, when one or more of $R_1$-$R_4$ in the product comprises a hydroxyl group, one or more of $R_1$-$R_4$ can be protected with a suitable hydroxyl protecting group during steps (a)-(c) and then deprotected. In some embodiments, the protecting group can be an acyl group (i.e., —C(=O)$CH_3$) which can be removed under various conditions as known in the art. See e.g., Greene et al. (1999) "Protective Groups in Organic Chemistry," Third Edition, John Wiley & Sons, Inc., New York. In some embodiments, one or more acyl protecting groups are removed by contacting the initially formed conjugated ketone with a base (e.g., an alkali metal hydroxide, such as LiOH, NaOH, or KOH). In some embodiments, step (a) is performed in a non-polar, aprotic solvent, such as tetrahydrofuran, and/or at a temperature below room temperature (e.g., about −78° C.). In some embodiments, step (b) is performed in an aromatic solvent (e.g., benzene or toluene) or other non-polar, aprotic solvent. In some embodiments, step (b) is performed at a temperature above room temperature (e.g. at between about 60° C. and about 120° C.). Suitable aromatic aldehydes and methyl ketones can be obtained commercially or prepared as described in the literature. In some embodiments, the methyl ketone is 3-nonene-2-one.

In some embodiments, the presently disclosed subject matter provides a method of preparing a compound having a structure of one of the formulas:

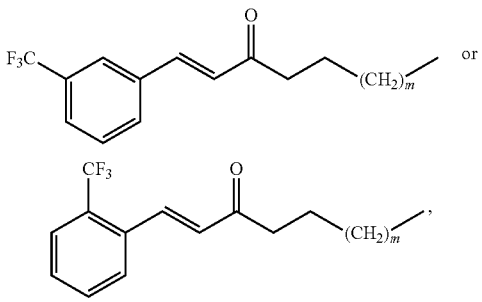

wherein m is 0-4, wherein the method comprises performing a mixed aldol condensation between an aromatic aldehyde and a methyl ketone and, if necessary, dehydrating a resulting alcohol intermediate. In some embodiments, the method comprises (a) providing an aromatic aldehyde having a structure of the formula:

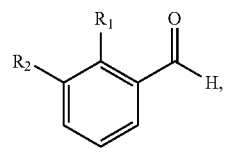

wherein $R_1$ is —H and $R_2$ is —$CF_3$ or wherein $R_1$ is —$CF_3$ and $R_2$ is —H; (b) contacting the aromatic aldehyde with an enolate formed by reacting a base, such as an alkyl lithium (e.g., n-butyl lithium (n-BuLi), LDA (lithium diisopropylamide), LiHMDS (lithium bis(trimethylsilyl)amide), or NaH, with a methyl ketone having a structure of the formula:

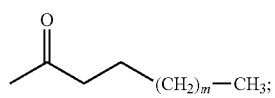

wherein m is an integer between 0 and 4, thereby providing an alcohol having a structure of the formula:

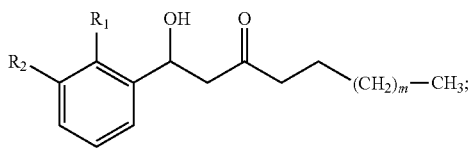

and (c) contacting the alcohol formed in step (b) with an suitable acid (e.g., PTSA) to dehydrate the alcohol to form a double bond (i.e., between the aromatic ring and the ketone moiety), thereby providing a conjugated ketone.

In some embodiments, step (a) is performed in a non-polar, aprotic solvent, such as tetrahydrofuran, and/or at a temperature below room temperature (e.g., about −78° C.). In some embodiments, step (b) is performed in an aromatic solvent (e.g., benzene or toluene) or other non-polar, aprotic solvent. In some embodiments, step (b) is performed at a temperature above room temperature (e.g. at between about 60° C. and about 120° C.). Suitable aldehydes and methyl ketones for the methods can be obtained commercially or prepared as described in the literature. In some embodiments, the methyl ketone is 2-nonanone.

In one aspect, the presently disclosed subject matter provides a method of treating a disease associated with inflammation and/or oxidative stress in a subject in need thereof, wherein the disease is treatable by the activation of Nrf2, wherein the method comprises administering to the subject a therapeutically effective amount of a compound having a structure of the formula:

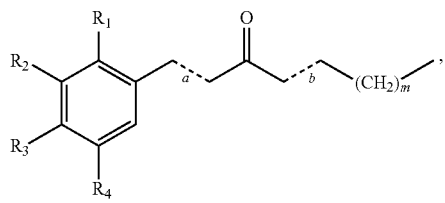

wherein: 'a' and 'b' are each independently a single bond or a double bond; m is an integer between 0 and 4; $R_1$ is —H, halogen, halogen-substituted $C_1$-$C_4$ alkoxy, —COOH, or halogen-substituted $C_1$-$C_4$ alkyl; $R_2$ is —H, halogen, —OH, halogen-substituted $C_1$-$C_4$ alkoxy, —COOH, or halogen-substituted $C_1$-$C_4$ alkyl; and $R_3$ and $R_4$ are independently selected from the group comprising —H, —OH, amino, $C_1$-$C_4$ alkyl, $C_1$-$C_4$ alkylamino, and $C_1$-$C_4$ alkoxy, subject to the proviso that when $R_1$ and $R_2$ are each —H, $R_3$ and $R_4$ are each independently selected from —OH and $C_1$-$C_4$ alkoxy, and subject to the proviso that when $R_4$ is methoxy, $R_1$ is —H, $R_2$ is —H, 'a' is a single bond, and 'b' is a double bond, $R_3$ is $C_1$-$C_4$ alkoxy; or a pharmaceutically acceptable salt thereof. In some embodiments, the compound is other than 6S (i.e., the compound wherein 'a' is a single bond; 'b' is a double bond, $R_1$ and $R_2$ are each —H, $R_3$ is —OH, and $R_4$ is OMe). In some embodiments, when 'a' is a single bond, 'b' is a double bond, $R_1$ and $R_2$ are each —H, and $R_4$ is —OMe, $R_3$ is $C_1$-$C_4$ alkoxy. In some embodiments, when 'a' is a single bond, 'b' is a double bond, $R_1$ and $R_2$ are each —H, and $R_4$ is —$C_1$-$C_4$ alkoxy, $R_3$ is $C_1$-$C_4$ alkoxy.

In some embodiments, the compound is not a compound wherein 'a' is a single bond, 'b' is a double bond and $R_1$ and $R_2$ are each —H. In some embodiments, 'a' is not a single bond when 'b' is a double bond. In some embodiments, 'a' and 'b' are both double bonds, both single bonds, or 'a' is a double bond and 'b' is a single bond.

In one variation of any embodiment or aspect disclosed herein, the method comprises administering a compound wherein m is 0, 2 or 4. Alternately, m is 4.

In some embodiments, $R_1$ is selected from —H, halogen, —OCF$_3$, —OCHF$_2$, —COOH, and —CF$_3$. In some embodiments, $R_1$ is selected from —H, —F, —OCF$_3$, and —CF$_3$. In some embodiments, $R_1$ is selected from —H, —F, and —CF$_3$. In some embodiments, $R_2$ is selected from —H, halogen, —OH, —OCF$_3$, and —CF$_3$. In some embodiments, $R_2$ is selected from —H, —F, —OH, and —CF$_3$.

In another embodiment, the method comprises administering a compound wherein 'a' and 'b' are each a single bond. In another embodiment, $R_1$ and $R_2$ are each —H; m is 4; and the method comprises administering a compound having a structure of the formula:

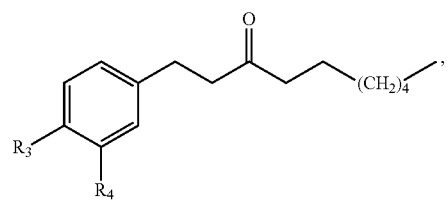

wherein $R_3$ and $R_4$ are each independently selected from the group of —OH, —OMe, —OEt, —O$^i$Pr, —O$^n$Pr, —O$^n$Bu, —O$^i$Bu, —O$^t$Bu, and —O$^s$Bu. In another embodiment, $R_3$ is —OH and $R_4$ is —OMe.

In another embodiment the method comprises administering a compound wherein 'a' is a double bond and 'b' is a single bond. In another embodiment, $R_1$ and $R_2$ are each —H; m is 4; and the method comprises administering a compound having a structure of the formula:

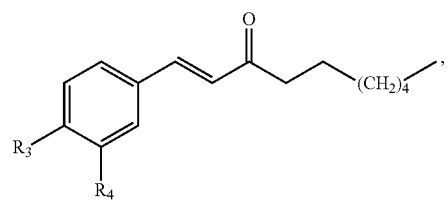

wherein each of $R_3$ and $R_4$ is independently selected from the group of —OH, —OMe, —OEt, —O$^i$Pr, —O$^i$Pr, —O$^n$Bu, —O$^n$Bu, —O$^i$Bu, and —O$^s$Bu. In yet another embodiment, each of $R_3$ and $R_4$ is independently selected from the group of —OH, —OMe, —OEt, —O$^i$Pr, and —O$^n$Pr. In yet another embodiment, $R_3$ is —OH and $R_4$ is —OH.

In another embodiment the method comprises administering a compound wherein 'a' and 'b' are each a double bond. In yet another embodiment, $R_1$ is —H; m is 4; and the method comprises administering a compound of having a structure of the formula:

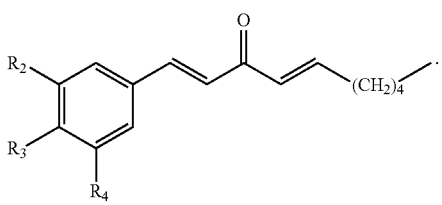

In another embodiment the method comprises administering a compound wherein $R_2$ is —H; and each of $R_3$ and $R_4$ is independently selected from the group of —OH, —OMe, —OEt, —O$^i$Pr, —O$^n$Pr, —O$^n$Bu, —O$^i$Bu, and —O$^s$Bu. Alternately, each of $R_3$ and $R_4$ is independently selected from the group of —OH, —OMe, —OEt, —O$^i$Pr, and —O$^n$Pr. In one variation, $R_3$ is —OH. In another variation, $R_4$ is —OMe. In yet another variation, $R_4$ is —OH.

The subject can be any vertebrate (e.g., a fish, mammal, bird, reptile, or amphibian). Thus, the instant methods can be used in medical and veterinary applications. In some embodiments, the subject is a mammal. In some embodiments, the subject is a human.

In some embodiments, the disease is a disease that is treatable (e.g., known to be treatable) via activation of Nrf2. In some embodiments, the disease is selected from the group comprising atherosclerosis, autoimmune diseases (e.g., rheumatoid arthritis (RA), lupus, psoriasis, multiple sclerosis (MS), etc.), neurodegenerative diseases (e.g., Alzheimer's disease or Parkinson's disease), chronic organ failure (e.g., renal failure, heart failure, or liver failure), systemic cardiovascular disease, chronic kidney disease, inflammatory bowel disease (IBD); osteoarthritis; osteoporosis; cystic fibrosis, diabetes, and diabetes-related diseases. In some embodiments, the disease is diabetes or a diabetes-related disease. In some embodiments the diabetes-related disease is selected from the group including, but not limited to, retinopathy, neuropathy, cardiomyopathy, and pancreatic damage.

The compound can be administered via any suitable route, e.g., orally, intravenously, topically, nasally, intramucosally, intraarterially, subcutaneously, intramuscularly, etc. In some embodiments, the compound can be administered orally as part of a nutraceutical composition.

As shown herein, the presently disclosed compounds, in some embodiments, comprising both an α,β-unsaturated carbonyl entity and a catechol moiety or its derivatives, enhance the Tg(gstp1:GFP) fluorescence signal in zebrafish embryos. Without being bound by theory, chemical reaction and in vivo metabolism studies of the potent 6S derivatives showed that both the α,β-unsaturated carbonyl entity and the catechol moiety or catechol derivative act as active groups for conjugation with the sulfhydryl groups of the cysteine residues in Keap1. In addition, 6S derivatives increased the expression of Nrf2 downstream target, heme oxygenase-1 (HO-1), in both a dose- and time-dependent manner. The α,β-unsaturated carbonyl entity and the catechol moiety or catechol derivative in the presently disclosed compounds can react with the cysteine residues of Keap1, disrupting the Keap1-Nrf2 complex, thereby liberating and activating Nrf2.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods and Materials

Anhydrous chemical reactions were carried out in oven-dried glassware under a nitrogen atmosphere unless otherwise noted. Reactions were monitored by analytical thin-layer chromatography (TLC) on 250 μm silica gel plates (GF254) (Merck Millipore, Burlington, Mass., United States of America) and visualized under UV light. The products were isolated and purified by either preparative TLC on 1000 μm silica gel plates (GF254) (Sorbent Technologies, Norcross, Ga., United States of America, catalog no. 1617124) or column chromatography (CC) using silica gel (Sorbent Technologies, Norcross, Ga., United States of America, catalog no. 3093M-25). $^1$H, $^{13}$C NMR, and two-dimensional (2-D) NMR spectra were recorded on a Bruker AVANCE 400 MHz or 600 MHz spectrometer (Bruker, Inc., Silberstreifen, Rheinstetten, Germany) using TMS as an internal standard. Chemical shifts (δ) are expressed in ppm. Coupling constants (J) are expressed in Hz, and multiplicities are indicated by s (singlet), d (doublet), t (triplet), q (quartet), and br (broad). The $^{13}$C NMR spectra are proton decoupled. Shogaols (1-3) and gingerols (11-13) used in the present study were purified from ginger extract. See Zhu et al. (2013) "Metabolites of ginger component [6]-shogaol remain bioactive in cancer cells and have low toxicity in normal cells: chemical synthesis and biological evaluation." *PLoS One* 8, e54677. 6S metabolites, 4-10, 14-17 and 25 were obtained from [6]-shogaol as described previously. See Zhu et al. (2013) *PLoS One* 8, e54677. Other chemicals were purchased from Sigma-Aldrich (St. Louis, Mo., United States of America) and were used without further purification. All compounds used were >95% pure. Fetal bovine serum and penicillin/streptomycin were purchased from Gemini Bio-Products (West Sacramento, Calif., United States of America). Human normal colonic epithelial cells (CCD 841 CoN, ATCC® CRL-170™) were obtained from ATCC (Manassas, Va., United States of America).

Statistical Analysis.

All results are presented as means±standard deviation. An unpaired t test was used to determine potential differences between each treatment and control. Comparisons between all treatments and control were measured by one way ANOVA with Dunnett's test using the GraphPad Prism version 5.04. A p value of less than 0.05 was considered statistically significant in all tests.

Example 2

Synthesis of 161-Shogaol Derivatives

Aryl-1,4-dien-3-ones, typical Michael acceptors, can be synthesized by Horner-Emmons olefination of 2-oxo-3-alkenylphosphonates with benzaldehydes in the presence of lithium bromide and triethylamine, (see Tsuge, O., Kanemasa, S., Nakagawa, N., and Suga, H. (1987) "Horner-Emmons olefination of 4-hydroxy-2-oxoalkyl-phosphonates and related compounds: applications to the synthesis of (±)-gingerol, (±)-yashabushiketol, and (±)-dihydroyashabushiketol." *Bull. Chem. Soc. Jpn.* 60, 4091-4098) or by conjugate addition of vinyl iodide to styryl-activated enones under n-BuLi (see Sieber, J. D., Liu, S., and Morken, J. P. (2007) "Catalytic conjugate addition of allyl groups to styryl-activated enones." *J. Am. Chem. Soc.* 129, 2214-2215 or Sieber, J. D., and Morken, J. P. (2008) "Asymmetric Ni-catalyzed conjugate allylation of activated enones." *J. Am. Chem. Soc.* 130, 4978-4983).

Disclosed herein is a straightforward strategy to synthesize aryl-dec-1,4-dien-3-ones (6S derivatives), using commercial aromatic aldehydes and low reactive species 3-nonen-2-one via nucleophilic addition and subsequent dehydration. In short, the appropriate substituted aromatic aldehydes (32a-g) were treated with lithium species of 3-nonen-2-one to form β-hydroxyenones (33a-g), and then a rapid para-toluene sulfonic acid (PTSA)-catalyzed dehydration was followed, furnishing the target [6]-dehydroshogaol derivatives (18, 20-24 and 26). See Scheme 1A, below. M14-4 analogues are based on the core structure of M14-4 (21). M14-4A-B probe the bioactivity effects of lipophilicity in the side chain, while M14-4C-J probe the bioactivity effects of substitutions on aromatic ring. See Scheme 1B, below. Analogously, M14-9 analogues, i.e., M14-9A-E, are based on the core structure of M14-4 and probe the effect of double bonds in the side chain. See Scheme 1C, below.

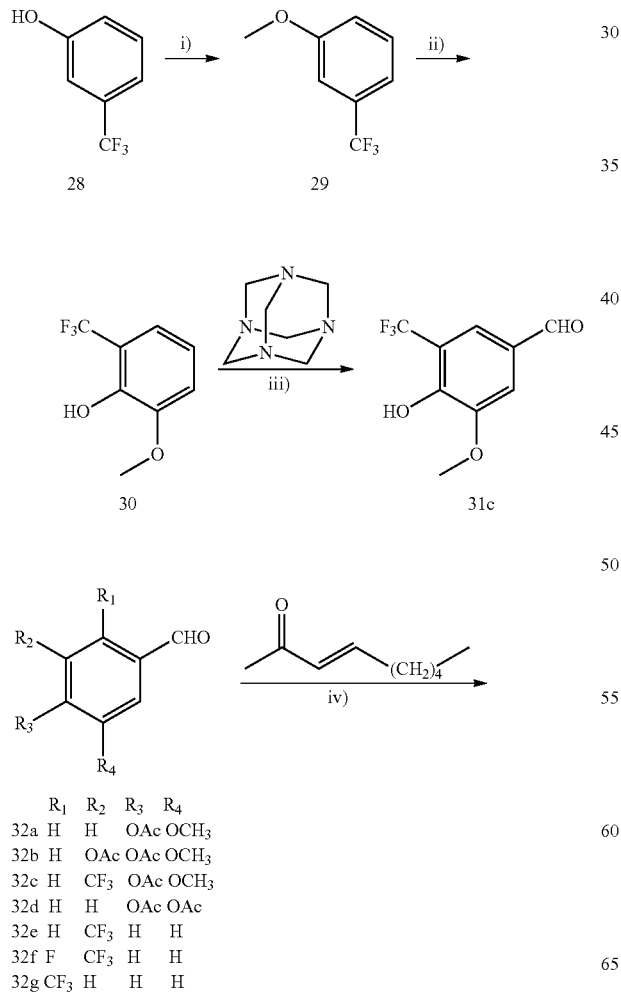

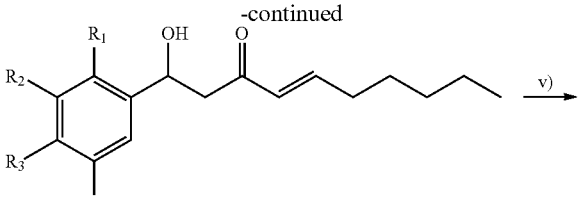

| | $R_1$ | $R_2$ | $R_3$ | $R_4$ |
|---|---|---|---|---|
| 33a | H | H | OAc | OCH$_3$ |
| 33b | H | OAc | OAc | OCH$_3$ |
| 33c | H | CF$_3$ | OAc | OCH$_3$ |
| 33d | H | H | OAc | OAc |
| 33e | H | CF$_3$ | H | H |
| 33f | F | CF$_3$ | H | H |
| 33g | CF$_3$ | H | H | H |

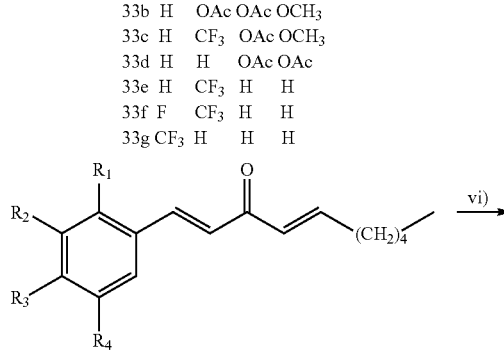

| | $R_1$ | $R_2$ | $R_3$ | $R_4$ |
|---|---|---|---|---|
| 34a | H | H | OAc | OCH$_3$ |
| 34b | H | OAc | OAc | OCH$_3$ |
| 34c | H | CF$_3$ | OAc | OCH$_3$ |
| 34d | H | H | OAc | OAc |
| 22 | H | CF$_3$ | H | H |
| 23 | F | CF$_3$ | H | H |
| 24 | CF$_3$ | H | H | H |

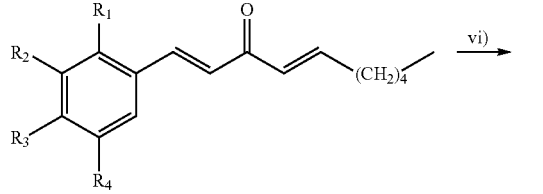

| | $R_1$ | $R_2$ |
|---|---|---|
| 18 | H | OCH$_3$ |
| 20 | OH | OCH$_3$ |
| 21 | CF$_3$ | OCH$_3$ |
| 26 | H | OH |

Scheme 1A. Synthesis of aldehyde (31c) and [6]-dehydroshogaol derivatives (18, 20-24, and 26). Regents and conditions: i) CH$_3$I, K$_2$CO$_3$, acetone, 0°C.-rt, 18 h, yield 100%; ii) n-BuLi, THF, -78°C.-rt, 25 min; B(OMe)$_3$, -78°C.-rt, 18h; NH$_3$ in MeOH; and then H$_2$O$_2$, 0°C.-rt, 2 h, yield 50%; iii) hexamethylenetetramine, TFA, reflux, 3 h, yield 20%; iv) trans-3-none-2-one, n-BuLi, DIPA, THF, -78°C., 35 min, yield 34-90%; v) PTSA toluene, reflux, 5 min, yield 36-86%; vi) LiOH, THF/MeOH/H$_2$O, 5 min, yield 59-83%.

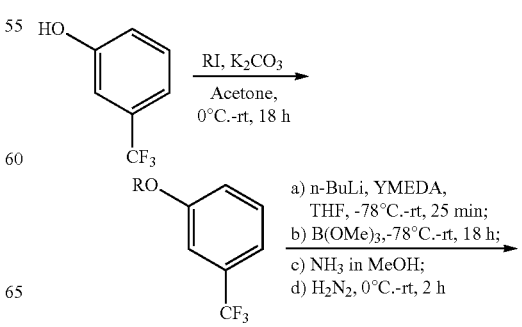

a) n-BuLi, YMEDA, THF, -78°C.-rt, 25 min;
b) B(OMe)$_3$,-78°C.-rt, 18 h;
c) NH$_3$ in MeOH;
d) H$_2$N$_2$, 0°C.-rt, 2 h

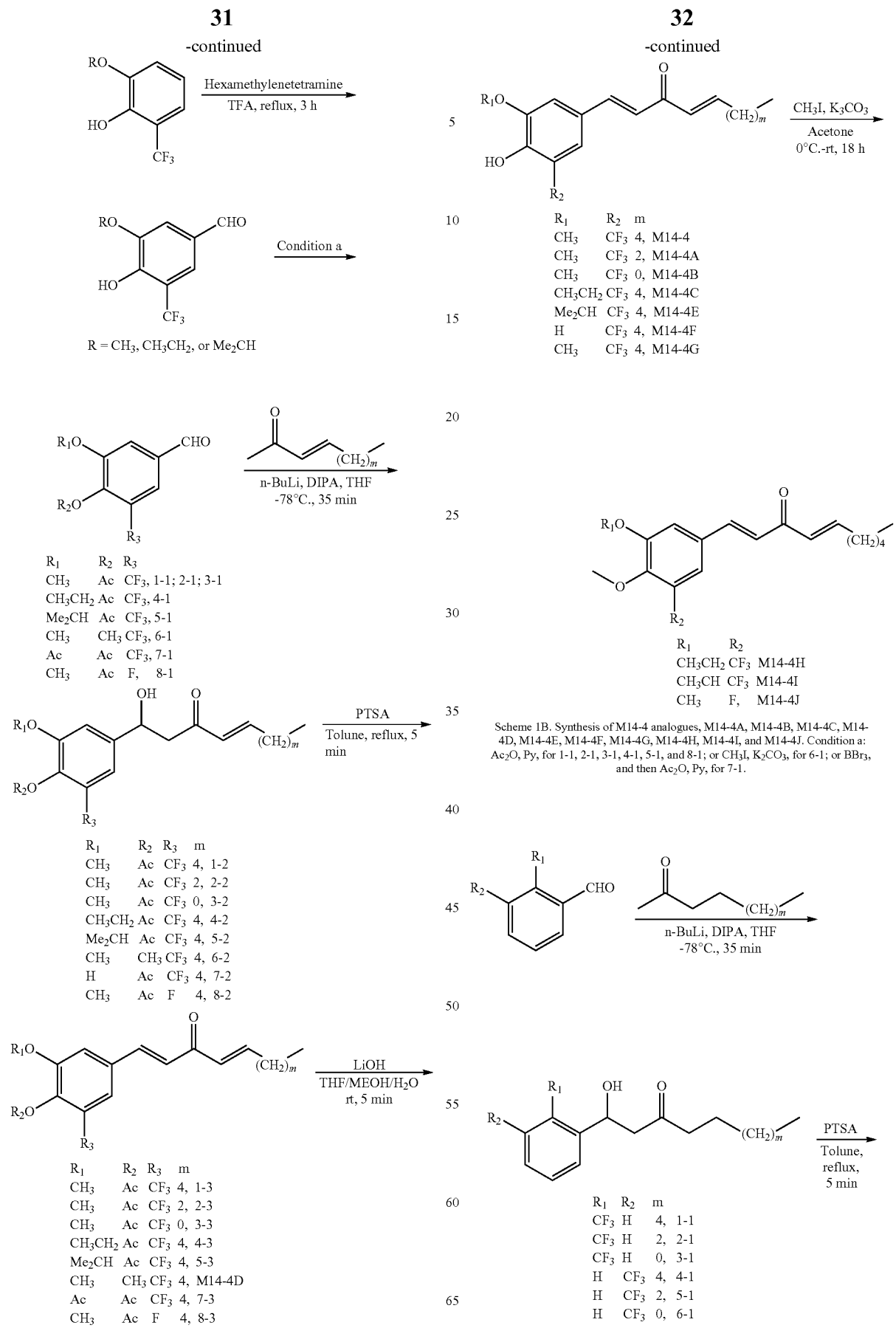

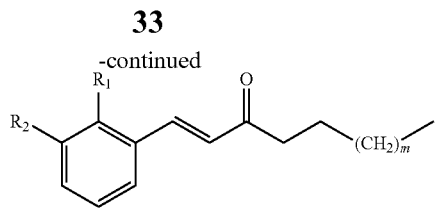

| R₁ | R₂ | m | |
|---|---|---|---|
| CF₃ | H | 4, | M14-9 |
| CF₃ | H | 2, | M14-9A |
| CF₃ | H | 0, | M14-9B |
| H | CF₃ | 4, | M14-9C |
| H | CF₃ | 2, | M14-9D |
| H | CF₃ | 0, | M14-9E |

Scheme 1C. Synthesis of M14-9 and its analogues, M14-9A, M14-9B, M14-9C, M14-9D, and M14-9E.

Likewise, [6]-dehydroparadol derivatives (19 and 27) were successfully prepared using aromatic aldehydes (32a and 32d) and low reactive lithium species of 2-nonanone. See Scheme 2, below. Non-commercially available aldehyde 31c was prepared from 3-(trifluoromethyl)phenol following the steps as reported in Backstrom, R., Honkanen, E., Pippuri, A., Kairisalo, P., Pystynen, J., Heinola, K., Nissinen, E., Linden, I. B., Mannisto, P. T., Kaakkola, S., and et al. (1989) "Synthesis of some novel potent and selective catechol O-methyltransferase inhibitors." *J. Med. Chem.* 32, 841-846. Cysteinyl conjugates 35 and 36 were made under Michael addition conditions according to the method for the preparation of cysteine conjugate of 6S. See Scheme 3A, below. Conjugate 37 was successfully synthesized through 2-iodoxybenzoic acid (IBX)-mediated oxidation to the o-quinone followed by nucleophilic addition of L-cysteine. See Scheme 3A. See also De Lucia, M., Panzella, L., Pezzella, A., Napolitano, A., and d'Ischia, M. (2008) "Plant catechols and their S-glutathionyl conjugates as antinitrosating agents: expedient synthesis and remarkable potency of 5-S-glutathionylpiceatannol." *Chem. Res. Toxicol.* 21, 2407-2413). The compounds were confirmed by $^1$H and $^{13}$C NMR spectroscopy, and LC-ESI/MS. All final products are >95% pure.

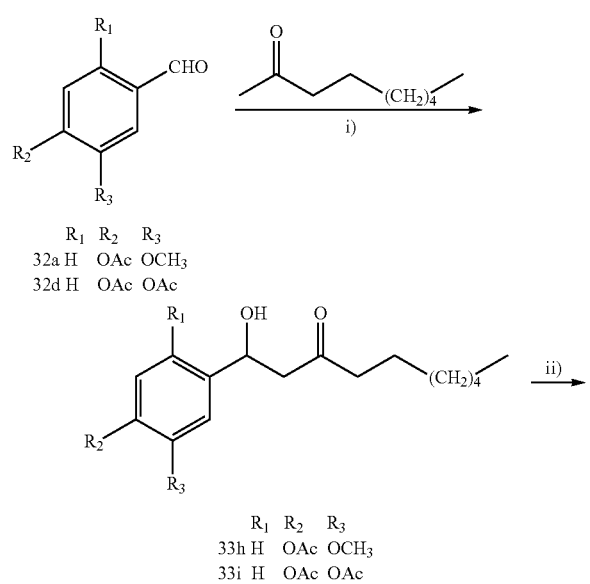

| | R₁ | R₂ | R₃ |
|---|---|---|---|
| 32a | H | OAc | OCH₃ |
| 32d | H | OAc | OAc |

| | R₁ | R₂ | R₃ |
|---|---|---|---|
| 33h | H | OAc | OCH₃ |
| 33i | H | OAc | OAc |

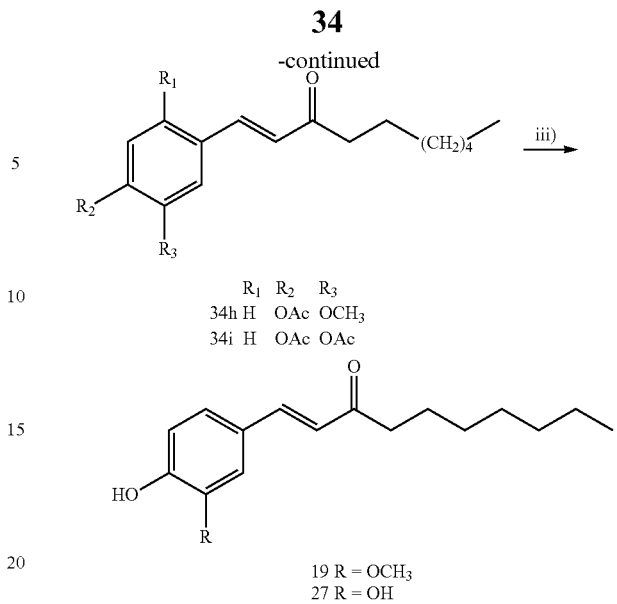

| | R₁ | R₂ | R₃ |
|---|---|---|---|
| 34h | H | OAc | OCH₃ |
| 34i | H | OAc | OAc |

19 R = OCH₃
27 R = OH

Scheme 2. Synthesis of [6]-dehydroparadol derivatives (19 and 27). Regents and conditions: i) 2-nonanone, n-BuLi, DIPA, THF, -78°C., 35 min, yield 32-85%; ii) PTSA, toluene, reflux, 5 min, yield 41-68%; ii) LiOH, THF/MeOH/H2O, rt, 5 min, yield 79-80%.

Example 3

Studies with Transgenic Zebrafish and Embryos

The Keap1-Nrf2 system is conserved among vertebrates, including zebrafish. Zebrafish Nrf2 protein shares six highly conserved Neh domains with mammalian Nrf2 proteins, which are considered to play critical functions in Nrf2 regulation. Zebrafish has been shown to be a powerful tool to analyze the molecular basis of the Nrf2-Keap1 system. In particular, a green fluorescent protein (GFP) reporter gene driven by the gstp1 promoter was created in the Tg(gstp1: GFP) transgenic zebrafish and provides a new and attractive platform to screen novel Nrf2 activators in vivo for drug discovery.

Transgenic Zebrafish and Embryos.

Zebrafish AB transgenic strains Tg(gstp1:GFP) were maintained in a Pentair Aquatic Ecosystem (Apopka, Fla., United States of America) fish housing unit with 14 h light/10 h dark cycle (see Tsujita, T., Li, L., Nakajima, H., Iwamoto, N., Nakajima-Takagi, Y., Ohashi, K., Kawakami, K., Kumagai, Y., Freeman, B. A., Yamamoto, M., and Kobayashi, M. (2011) "Nitro-fatty acids and cyclopentenone prostaglandins share strategies to activate the Keap1-Nrf2 system: a study using green fluorescent protein transgenic zebrafish." *Genes Cells* 16, 46-57). The fish embryos were maintained at 28.5° C. in 0.3× Danieau's solution (19.3 mM NaCl, 0.23 mM KCl, 0.13 mM MgSO₄, 0.2 mM Ca(NO₃)₂, 1.7 mM HEPES, pH 7.0) containing 30 µg/ml phenylthiourea (PTU) to inhibit pigmentation. Tg(gstp1:GFP) cross with AB wild-type strain fluorescence embryos were used for the experiment. Zebrafish embryos were washed, dechorionated and anaesthetized before observations, and fluorescence imaging for analysis.

Chemical Treatments.

Transgenic zebrafish embryos at 1 day-post-fertilization (dpf) were dechorionated and placed in Petri dishes containing different chemicals diluted in 0.3× Danieau's solution containing PTU. The chemical stock was dissolved in DMSO at 5 mM concentration. The control contains DMSO at the corresponding concentration of 0.1% which showed no effect on embryonic development and no effect on Tg(gstp1:GFP) fluorescence activity.

Fluorescent Imaging.

An Olympus MVX10 Fluorescence Macroscope (Olympus, Center Valley, Pa., United States of America) equipped with a Hamamatsu C9300-221 high-speed digital CCD camera (Hamamatsu City, Japan) was used for fluorescence microscopy. Tg(gstp1:GFP) fluorescent embryos were anaesthetized in tricaine and imaged at 2 dpf. MetaMorph Basic software (Olympus, Center Valley, Pa., United States of America) was used for image acquisition and analysis.

Quantification of Nrf2 Reporter Activity by Tg(gstp1:GFP) Fluoresence in Zebrafish Model.

The fluorescence intensity of the olfactory neural epithelia was quantitated using MetaMorph Basic software. In brief, GFP expression in the olfactory regions of Tg(gstp1:GFP) embryos treated with various chemicals was measured after 24-hour treatment from 1 dpf to 2 dpf. The GFP induction was detectable by fluorescence signal at the area of the olfactory epithelia in the anterior of the head region, the intensity was measured using an area of a circle of 60 pixel diameter of the fluorescence olfactory epithelia subtracted by a background non-fluorescence area next to the zebrafish embryo. Both the left and right olfactory epithelia were measured to give an average fluorescence value. The values are an average of measurements from at least 10 embryos.

Measurement of Reactive Oxygen Species (ROS).

Zebrafish embryos (20/group) at 1 dpf were dechorionated, and treated with 5 µM compounds 1, 18, 26, and 27 over 2, 4, 8, and 24 h. The embryos at each time point were then used for ROS extraction and analysis. The ROS assay employed the cell-permeable fluorogenic probe 2', 7'-dichlorodihydrofluorescindiacetate (DCFH-DA; Sigma Aldrich, St. Louis, Mo., United States of America) to measure the relative changes in $O^-_2$ and $H_2O_2$ levels in Zebrafish embryos after treatment. All the Zebrafish embryos were homogenized in 400 µL ice-cooled phosphate buffered saline (PBS), and 100 µL homogenate was added into the well of 96-well plate in triplicate (PBS was run as background). Each well was added 5 µL 20 mM DCFH-DA stock freshly prepared, and then the plate was incubated at 37° C. for 15, 30, and 60 min. The plate was immediately placed in a Biotek (Winooski, Vt., United States of America) microplate reader to measure fluorescence at wavelengths of 485 nm (excitation) and 528 nm (emission) at the given incubation time points. The protein concentrations of homogenate were determined using Bradford method. The corrected fluorescent values were calculated as the increase rate per minute per mg protein and normalized to respective control for each time point and are presented as fold induction (n=3).

Biotransformation of Xenobiotics 18 and 25-27 in Zebrafish Embryos.

Fifty zebrafish embryos at the 8 hour-post-fertilization (hpf) stage were incubated at 28.5° C. in 0.3× Danieau's solution (19.3 mM NaCl, 0.23 mM KCl, 0.13 mM $MgSO_4$, 0.2 mM $Ca(NO_3)_2$, 1.7 mM HEPES, pH 7.0) with or without 5 µM 18 and 25-27, respectively. At 24 hpf, embryos were dechorionated manually and the chorions were carefully removed one by one from the culture medium. The zebrafish embryos were harvested and kept at −80° C. till analyzed by LC/MS.

Zebrafish Embryo Sample Preparation.

200 µL Sodium acetate buffer solution (pH 5.0) was added to 50 zebrafish embryos. Samples were homogenized for 90 s by an Omni Bead Ruptor Homogenizer (Kennesaw, Ga., United States of America). 10 µL 10% ascorbic acid and 300 µL sodium acetate buffer were added to the homogenates. The mixture was incubated in the presence of β-glucuronidase (250 U) and sulfatase (3 U) at 37° C. for 45 min, and then 600 µL MeOH with 1% acetic acid was added. The resulting mixture was vortexed for 30 s and then centrifuged at 17000 g for 10 min. The supernatant was removed and evaporated under a gentle stream of nitrogen. The residue was reconstituted in 150 µL 90% MeOH with 0.2% acetic acid (AA), and 10 µL was analyzed directly by LC/MS.

LC/MS Analysis.

LC/MS analysis was carried out with a Thermo-Finnigan Spectra System, which consisted of an Accela high speed MS pump, an Accela refrigerated autosampler, and an LCQ Fleet ion trap mass detector (Thermo Electron, San Jose, Calif., United States of America) incorporated with an electrospray ionization (ESI) interface. A Gemini-NX $C_{18}$ column (150 mm×4.6 mm i.d., 5 µm; Phenomenex, Torrance, Calif., United States of America) was used for separation at a flow rate of 0.3 mL/min. The column was eluted with 100% A (5% aqueous methanol with 0.2% formic acid) for 1 min, followed by linear increases in B (95% aqueous methanol with 0.2% formic acid) to 55% from 1 to 4 min, to 85% from 4 to 25 min, then to 100% B from 25 to 30 min, and then with 100% B from 30 to 35 min. The column was then re-equilibrated with 100% A for 5 min. The LC eluent was introduced into the ESI interface. The positive ion polarity mode was set for the ESI source with the voltage on the ESI interface maintained at approximately 4.6 kV. Nitrogen gas was used as the sheath gas and auxiliary gas. Optimized source parameters, including capillary temperature (260° C.), sheath gas flow rate (31 arbitrary units), auxiliary gas flow rate (16 units), tube lens (34 V), and capillary voltage 9 V, were tuned using authentic samples. The collision-induced dissociation (CID) was conducted with an isolation width 2 Da and normalized collision energy of 35 for $MS^2$. The mass range was measured from 100 to 800 m/z. Data acquisition was performed with Xcalibur version 2.0 (Thermo Electron, San Jose, Calif., United States of America).

Example 4

Cell Studies

Western Blotting.

Human normal colonic epithelial cells (CCD 841 CoN) were grown in Eagle's Minimum Essential Medium with 10% fetal bovine serum and 1% penicillin/streptomycin, and maintained at 37° C. in a 100% humidified atmosphere of 5% $CO_2$ and 95% air. Fresh growth medium was added to the cells every two days until confluent. Cells were planted in 145×20 mm flat-bottomed tissue culture dishes and growth to 70-80% confluence and then treated with compound 27 for various doses and time points. At the end of incubation period, cell lysates were prepared in ice-cold Cell Lysis Buffer (Cell Signaling, Danvers, Mass., United States of America) with 1% protease inhibitor cocktail and 1% phenylmethylsulfonyl fluoride (Sigma, St. Louis, Mo., United States of America). Protein concentrations were measured using BCA Protein Assay Kit (Thermo Scientific, Rockford, Ill., United States of America). Aliquots containing 30 µg protein were loaded onto a 10-12% sodium dodecyl sulfatepolyacrylamide gel, transblotted onto polyvinylidene difluoride (PVDF) membrane (Bio-Rad Laboratories, Beverly, Calif., United States of America), blocked with Tris buffered saline with 1% Casein with 0.1% Tween- 20, and then incubated with each of the primary antibodies of HO-1 and β-actin overnight at 4° C. (Cell Signaling, Beverly, Mass., United States of America). The membrane was then incubated with horseradish peroxidase-conjugated donkey anti-rabbit IgG (Cell signaling, Danvers, Mass., United States of America). The bound complexes were detected with SuperSignal Chemiluminescent Substrate (Thermo Scientific, Rockford, Ill., United States of America). The immunoblot bands were quantified by densitometry analysis, and the ratio to β-actin was calculated and presented.

Growth Inhibitory Effects of 26 (M14-11) and 27 (M14-13) Against Human Colon Cancer Cells:

Cell viability was determined by an MTT colorimetric assay. Briefly, human colon cancer cells HCT-116 or HT-29, were plated in 96-well microtiter plates with 3000 cells/well and allowed to attach for 24 hours at 37° C. and 5% $CO_2$. The test compounds (in DMSO) were added to cell culture medium to desired final concentrations (final DMSO concentrations for control and treatments were 0.1%). After the cells were cultured for 24 hours, the medium was aspirated and cells were treated with 200 μL fresh medium containing 2.41 mmol/L MTT. After incubation for 3 hours at 37° C., the medium containing MTT was aspirated, 100 μL of DMSO was added to solubilize the formazan precipitate, and the plates were shaken gently for an hour at room temperature. Absorbance values were derived from the plate reading at 550 nm on a Biotek (Winooski, Vt., United States of America) microtiter plate reader. The reading reflected the number of viable cells and was expressed as a percentage of viable cells in the control. CCD-18Co cells were grown in EMEM. Both HCT-116 and HT-29 cells were cultured in McCoy's 5A medium. All of the above media were supplemented with 10% fetal bovine serum, 1% penicillin/streptomycin, and 1% glutamine, and the cells were kept in a 37° C. incubator with 95% humidity and 5% $CO_2$.

Example 5

Mouse Studies

Mouse Study.

Female C57BL/6J mice were purchased from the Jackson Laboratory (Bar Harbor, Me., United States of America) and allowed to acclimate for at least 1 week prior to the start of the experiment. The mice were housed 5 per cage and maintained in air-conditioned quarters with a room temperature of 20±2° C., relative humidity of 50±10%, and an alternating 12-h light/dark cycle. Mice were fed Rodent Chow #5001 (LabDiet, St. Louis, Mo., United States of America) and water, and were allowed to eat and drink ad libitum. Synthetic compounds 18 and 27 in DMSO were administered to mice by oral gavage (200 mg/kg), respectively. Urine samples were collected in metabolic cages (5 mice per cage) in 24 h after administration. The samples were stored at −80° C. until analysis.

Mouse Urine Sample Preparation.

Enzymatic deconjugation of mouse urine was performed as described previously with slight modifications. See J. D. Lambert, S. Sang, J. Hong, S. J. Kwon, M. J. Lee, C. T. Ho, C. S. Yang, "Per-acetylation as a means of enhancing in vitro bioactivity and bioavailability of epigallocatechin-3-gallate," Drug Metab Dispos 34 (2006) 2111-2116. In brief, triplicate samples were prepared in the presence of β-glucuronidase (250 U) and sulfatase (3 U) for 1.0 h at 37° C. After incubation, 500 μL methanol containing 0.2% AA was added to the medium. The resulting suspension was centrifuged at 17,000 g for 5 min, and 10 μL of supernatant was analyzed directly by LC/MS.

Example 6

Discussion of Examples 3-5

Potency of 6S Derivatives to Activate Nrf2 in Transgenic Zebrafish Embryos.

Figure 2A:
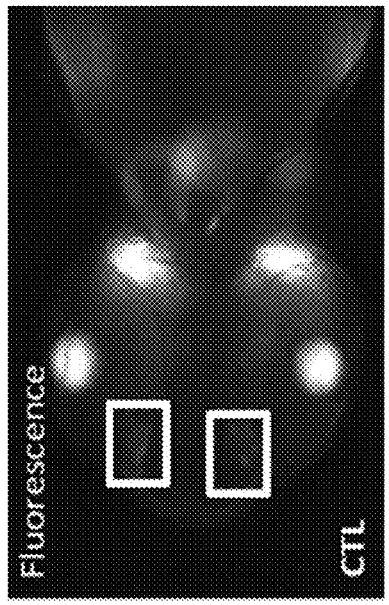
FIG. 2A is a bright field (without fluorescence) control (CTL) image of the ventral view of the head region of a zebrafish embryo.
Figure 2B:
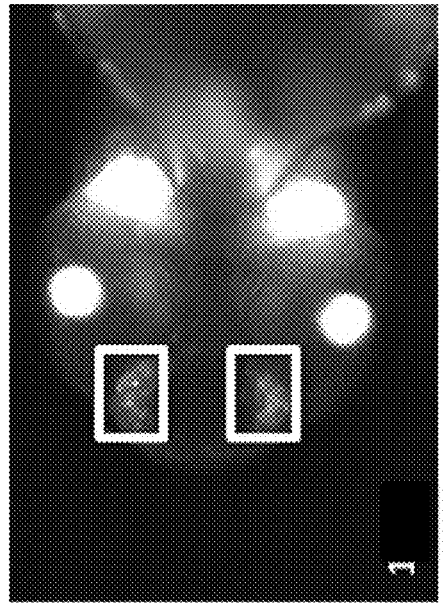
FIG. 2B is a fluorescent image of the Tg(gstp1:GFP) fluorescence signal at the olfactory sensory neural epithelia of a zebrafish embryo two days after 24 hour (hr) treatment with vehicle (dimethylsulfoxide (DMSO)).
Figure 2C:
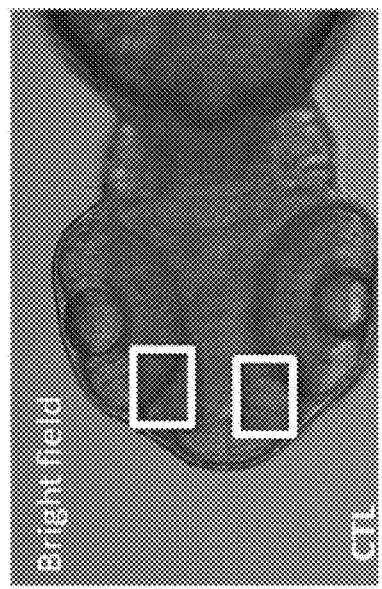
FIG. 2C is a fluorescent image of the Tg(gstp1:GFP) fluorescence signal at the olfactory sensory neural epithelia of a zebrafish embryo two days after 24 hour treatment with sulforaphane (SFN) at a concentration of 5 micromolar (μM). The inducible Tg(gstp1:GFP) activity at the olfactory sensory neural epithelia is indicated by the two rectangles.
Figure 2D:
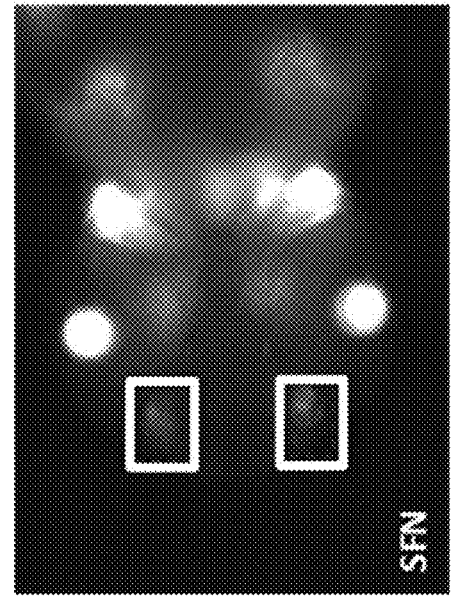
FIG. 2D is a fluorescent image of the Tg(gstp1:GFP) fluorescence signal at the olfactory sensory neural epithelia of a zebrafish embryo two days after 24 hour treatment with compound 1 (i.e., 6-shogaol (6S)) at a concentration of 5 micromolar (μM). The inducible Tg(gstp1:GFP) activity at the olfactory sensory neural epithelia is indicated by the two rectangles.

As shown in Table 1, below, 6S (1) is even more active than SFN, a well-known potent activator of Nrf2 (2.40 vs. 2.03 times higher than vehicle). Using quantitative microscopy, GFP fluorescence intensity at the olfactory sensory neural epithelia of 6S-treated zebrafish embryos was shown to be stronger than those of SFN-treated individuals. See also FIGS. 2C and 2D. Without being bound by theory, the α,β-unsaturated carbonyl entity in the side chain of 6S appears to play a role in Nrf2 activation.

TABLE 1

The Effects of 6S Derivatives on Tg(gstp1:GFP) fluorescence signal in Tg(gstp1:GFP) transgenic zebrafish embryos.

| Compound | Ratio/CTL |
|---|---|
| DMSO | 1.00 |
| SFN | 2.03 ± 0.49 |
| 1 | 2.40 ± 0.54 |
| 2 | 1.67 ± 0.55 |
| 3 | 1.53 ± 0.53 |
| 4 | 1.13 ± 0.21 |
| 5 | 1.27 ± 0.29 |
| 6 | 1.06 ± 0.20 |
| 7 | 1.04 ± 0.05 |
| 8 | 1.16 ± 0.47 |
| 9 | 0.93 ± 0.21 |
| 10 | 0.96 ± 0.24 |
| 11 | 1.87 ± 0.51 |
| 12 | 1.65 ± 0.29 |
| 13 | 1.29 ± 0.40 |
| 14 | 0.96 ± 0.21 |
| 15 | 1.08 ± 0.65 |
| 16 | 0.78 ± 0.12 |
| 17 | 0.72 ± 0.14 |
| 18 | 5.67 ± 0.59 |
| 19 | 3.29 ± 0.35 |
| 20 | 1.26 ± 0.14 |
| 21 | 2.18 ± 0.53 |
| 22 | 1.28 ± 0.10 |
| 23 | 1.63 ± 0.17 |
| 24 | 1.55 ± 0.67 |
| 25 | 4.32 ± 0.50 |
| 26 | 6.96 ± 0.48 |
| 27 | 9.19 ± 0.12 |

The activity of 6S was compared with its derivatives with the conversion of ketone group into hydroxyl group (4), the reduction of olefinic double bond (5), or both (14), as well as their related derivatives (6-10 and 15-17). The departure of the α,β-unsaturated carbonyl entity correlated with an attenuated Nrf2-induced activities. See FIG. 1 and Table 1. 6S demonstrated stronger activity than compounds 4 (1.13 times higher than vehicle) and 5 (1.27 times higher than vehicle), and compound 14 had no effect at all. See Table 1. Furthermore, thiol conjugation (6-9) also diminished the activity of 6S. 6G (11), the hydrated precursor of 6S, was also less potent than 6S (1.87 vs. 2.40 times higher than vehicle). See FIGS. 2D and 2E. The side chain length effect was investigated by comparing the effects of 6-, 8-, and 10-S (1-3) in Tg(gstp1: GFP) transgenic zebrafish embryos. The results indicate that the activities are in the order of 6S>8S>10S (2.40 vs. 1.67 vs. 1.53). See FIG. 1 and Table 1. A similar result was obtained for 6-G (11), 8-G (12), and 10-G (13) (1.87 vs. 1.65 vs. 1.29). See FIG. 1 and Table 1. This suggests that the lipophilicity of the alkyl tails in 6S derivatives diminishes the potency. Taken together, it appears that a compound comprising a central core consisting of an α,β-unsaturated carbonyl entity and a ten-carbon alkyl tail in 6S derivatives can exert potent Nrf2 activation and serve as a core structure to develop additional Nrf2 activators.

Recent studies have revealed that conjugated enones such as chalcones can stimulate expression of Nrf2-dependent genes such as HO-1, NQO-1, and GCLM, and are potent Nrf2 activators in vitro and in vivo. Conjugated 6S derivatives 18 and 19 were investigated and both compound 18, with a 1-aryl-1,4-dien-3-one entity in the structure, and compound 19, with a 1-aryl-1-en-3-one entity in the structure, were more potent than 6S (5.67 vs. 2.40 and 3.29 vs. 2.40), suggesting that conjugated unsaturated ketones in the side chains of 6S derivatives favor the activation of Nrf2.

Aside from the chemical modifications on the side chain, the electronic properties of the substituents on the aromatic rings of 6S derivatives were investigated. It was observed that an extra electron-donating group (—OH) at the C-5' position of the aromatic ring in 18, corresponding to 20, diminished the activity of 18 (1.26 vs. 5.67). See FIG. 1 and Table 1. Similarly, the introduction of an electron-withdrawing group (—CF$_3$) into the C-5' position of the ring in 18, corresponding to 21, also weakened the activity of 18, but had better activity than 20 (2.18 vs. 1.26). Removal of the hydroxyl and methoxyl groups from 21, corresponding to 22, further decreased the efficacy of 21 (1.28 vs. 2.18). Adding another electron-withdrawing group (—F) into the C-6' position of the ring in 22, corresponding to 23, or changing the substitution position of —CF$_3$, corresponding to 24, only slightly increased the activity of 22 (1.63 vs. 1.28 and 1.55 vs. 1.28). See FIG. 1 and Table 1.

Figure 2F:
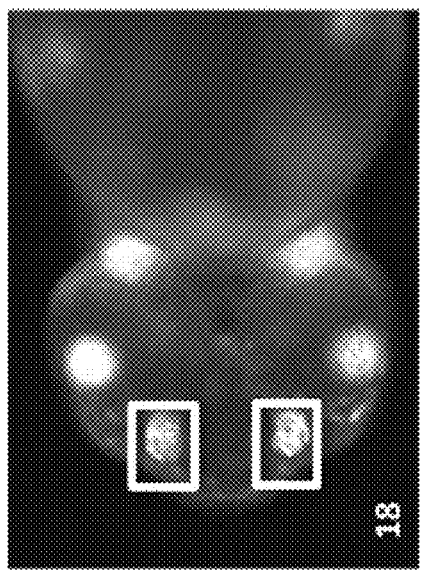
FIG. 2F is a fluorescent image of the Tg(gstp1:GFP) fluorescence signal at the olfactory sensory neural epithelia of a zebrafish embryo two days after 24 hour treatment with compound 18 at a concentration of 5 micromolar (μM). The inducible Tg(gstp1:GFP) activity at the olfactory sensory neural epithelia is indicated by the two rectangles.
Figure 2H:
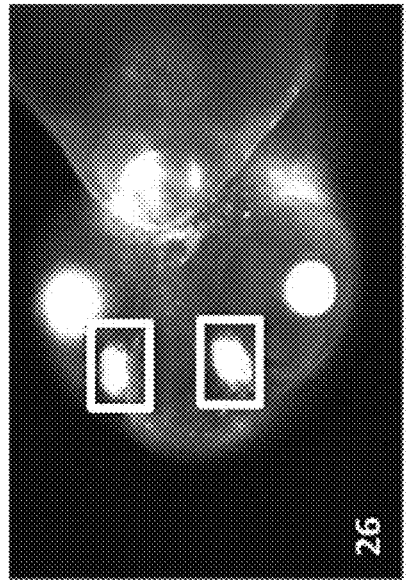
FIG. 2H is a fluorescent image of the Tg(gstp1:GFP) fluorescence signal at the olfactory sensory neural epithelia of a zebrafish embryo two days after 24 hour treatment with compound 26 at a concentration of 5 micromolar (μM) The inducible Tg(gstp1:GFP) activity at the olfactory sensory neural epithelia is indicated by the two rectangles.
Figure 2E:
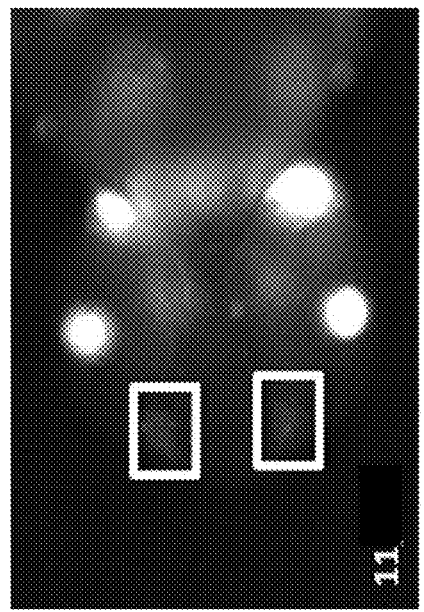
FIG. 2E is a fluorescent image of the Tg(gstp1:GFP) fluorescence signal at the olfactory sensory neural epithelia of a zebrafish embryo two days after 24 hour treatment with compound 11 (i.e., [6]-gingerol) at a concentration of 5 micromolar (μM). The inducible Tg(gstp1:GFP) activity at the olfactory sensory neural epithelia is indicated by the two rectangles.
Figure 2G:
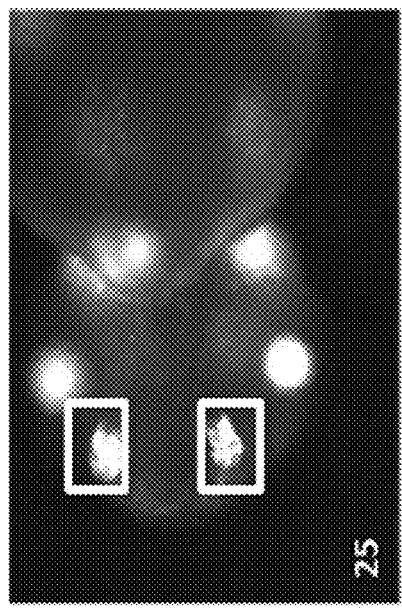
FIG. 2G is a fluorescent image of the Tg(gstp1:GFP) fluorescence signal at the olfactory sensory neural epithelia of a zebrafish embryo two days after 24 hour treatment with compound 25 at a concentration of 5 micromolar (μM). The inducible Tg(gstp1:GFP) activity at the olfactory sensory neural epithelia is indicated by the two rectangles.
Figure 2I:
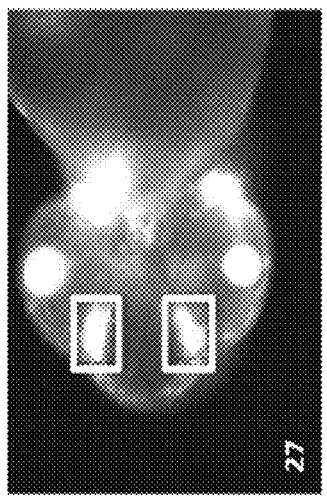
FIG. 2I is a fluorescent image of the Tg(gstp1:GFP) fluorescence signal at the olfactory sensory neural epithelia of a zebrafish embryo two days after 24 hour treatment with compound 27 at a concentration of 5 micromolar (µM). The inducible Tg(gstp1:GFP) activity at the olfactory sensory neural epithelia is indicated by the two rectangles.

Derivative 25, a metabolite of 6S, containing a catechol moiety and an isolated ketone group in the structure, exerted a comparable potency (4.32 times higher than vehicle) to conjugated enone 18 (5.67 times higher than vehicle) See FIGS. 1, 2F, and 2G, and Table 1. This suggests that a catechol moiety in the structure is can be an important factor for Nrf2 activation. Combination of a catechol moiety and an unsaturated carbonyl entity in a single molecule resulted in the synthesis of complexes of catechol and conjugated enone 26 and 27. See FIG. 1. Both 26 and 27 showed enhanced Nrf2-induced activity (6.96 times higher than vehicle for 26; and 9.19-fold higher than vehicle for 27), and were more active than conjugated enone 18 (5.67 times higher than vehicle), 19 (3.29 times higher than vehicle), and catechol 25 (4.32 times higher than vehicle). See FIGS. 1, 2F, 2G, 2H, and 2I, and Table 1. The activity of 27 was higher than the sum of 25 (4.32 times higher than vehicle) and 19 (3.29 times higher than vehicle), and the activity of 26 (6.96 times higher than vehicle) was also higher than 25 and 18. These findings suggest that the combination of a catechol moiety and a conjugated enone improves Nrf2-induced activity.

Compounds 18 and 25-27 were identified as potent Nrf2 activators in transgenic zebrafish embryos for the first time. Investigation of the structure activity relationship (SAR) of 6S derivatives demonstrated that 1) an α,β-unsaturated carbonyl entity in the alkyl tail is one factor in Nrf2 activation; 2) a conjugated unsaturated ketone in the structure enhances the activity; 3) a catechol moiety in the structure also plays a role in Nrf2-induced activities; and 4) coexistence of a catechol moiety and a conjugated unsaturated ketone in one molecule improves the activity. See Table 1 and FIGS. 1 and 2A-2I.

Effects of 6S and its Derivatives (18, 26, and 27) on Cellular Reactive Oxygen Species Levels.

Figure 3:
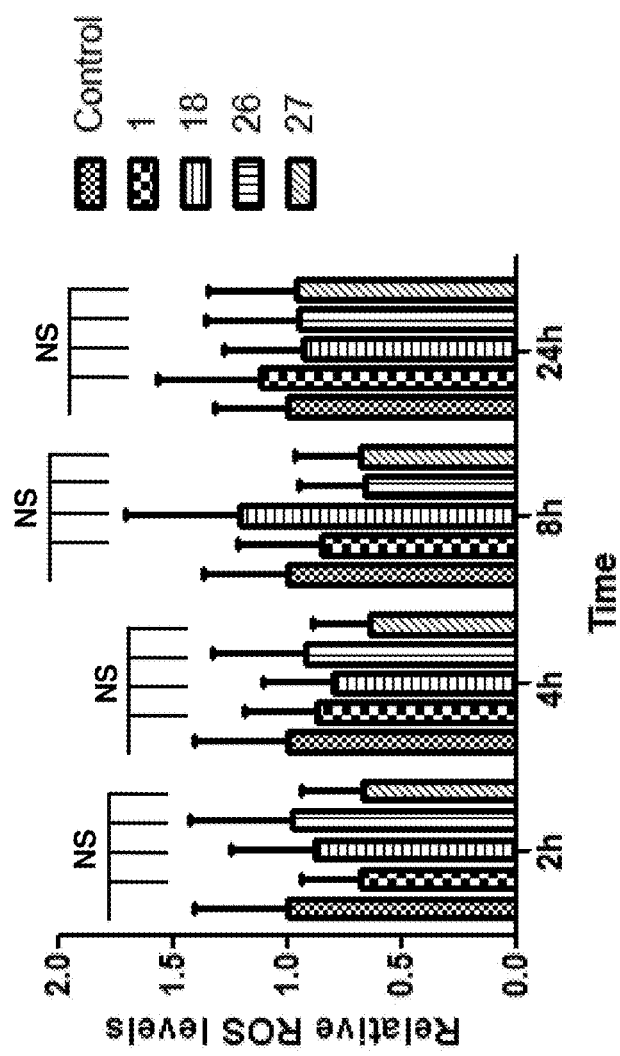
FIG. 3 is a graph of the effects of ROS (reactive oxygen species) production in zebrafish embryos by compounds 1, 18, 26 and 27. Zebrafish embryos at 1 day post fertilization (dpf) were treated with 5 micromolar (µM) concentrations of compounds 1, 18, 26, or 27 over 2, 4, 8, and 24 hours (h), and ROS levels in the embryos at each time point were measured using a cell-permeable fluorogenic probe, 2′, 7′-dichlorodihydrofluorescindiacetate (DCFH-DA). Data is also shown for embryos treated with vehicle (Control). One way ANOVA following Dunnett's test was used to determine the potential differences between all treatments and control. NS=no significant difference.

To determine whether ROS plays a role in the activation of Nrf2 pathway, the cellular ROS levels in zebrafish embryos treated with test agents were measured at 2, 4, 8, and 24 h. As shown in FIG. 3, the results indicate that these compounds did not induce oxidative stress, suggesting that ROS production is not one of the mechanism of actions of these derivatives.

6S Derivative (27) Increased HO-1 Expression in CCD 841 CoN Cells in Both a Dose-Dependent and Time-Dependent Manner.

Figure 4A:
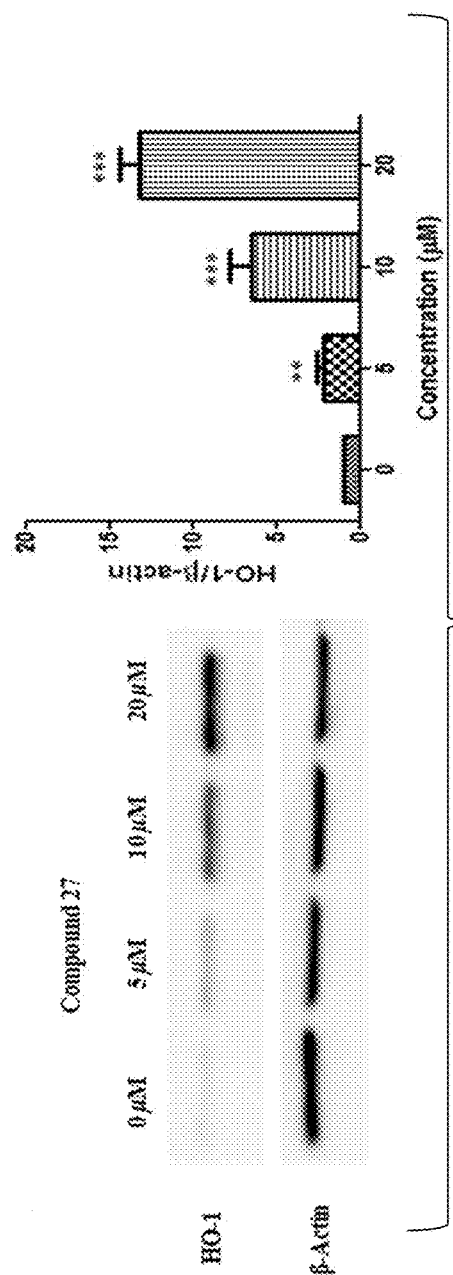
FIG. 4A shows the band of heme oxygenase-1 (HO-1) protein expression in a Western blot (left) and a graph of the effects of compound 27 on HO-1 expression in human normal colonic epithelial cells (CCD 841 CoN, ATCC® CRL-170™) (right). Compound 27 increased HO-1 expression in a dose-dependent manner. Cells were treated with 27 at concentrations of 0, 5, 10, and 20 micromolar (µM) for 24 hours (h), respectively. Proteins were loaded onto a 10-12% sodium dodecyl sulfatepolyacrylamide gel and then transblotted onto polyvinylidene difluoride membrane. β-Actin was used as an internal control. The fold changes in HO-1 expression are shown on the right at each row using densitometric analyses of the bands. Results are mean±SD (n=3). Bar, standard error; *=$p<0.05$; =$p<0.01$; *=$p<0.001$. All statistical tests are unpaired Student's t test, two-tailed, compared to control (0 µM).

Human normal colonic epithelial cells CCD 841 CoN were treated for 24 h with compound 27, the most active 6S derivative to activate Nrf2 in transgenic zebrafish embryos, at different doses of 5, 10, and 20 µM. As shown in FIG. 4A, 27 significantly increased HO-1 protein expression, compared to untreated control (p<0.05 for all concentrations). These data clearly illustrate that the representative 6S derivative 27 induces HO-1 expression in CCD 841 CoN cells in a dose-dependent manner.

Figure 4B:
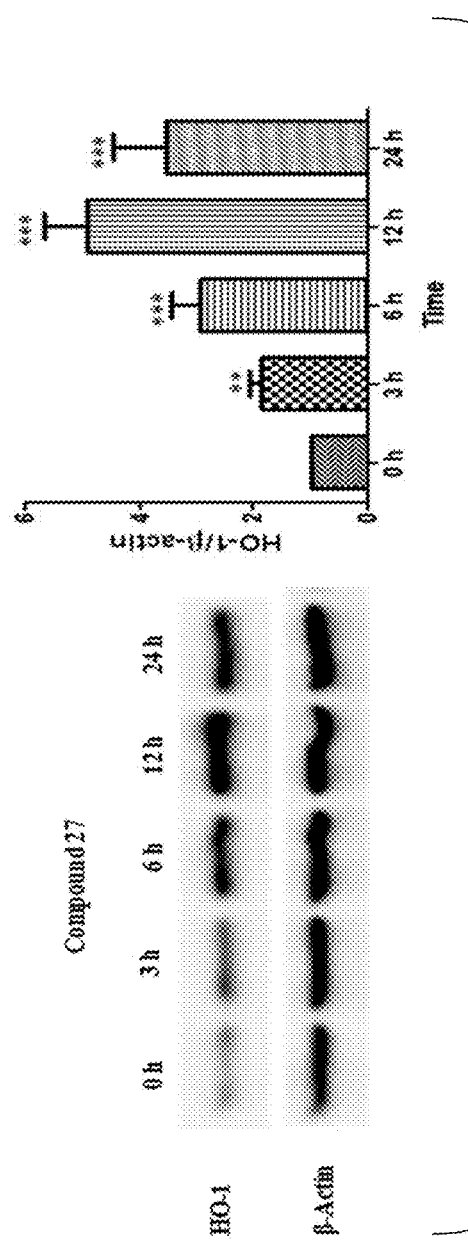
FIG. 4B shows the band of heme oxygenase-1 (HO-1) protein expression in a Western blot (left) and a graph of the effects of compound 27 on HO-1 expression in human normal colonic epithelial cells (CCD 841 CoN, ATCC® CRL-170™) (right). Compound 27 increased HO-1 expression in a time-dependent manner. Cells were treated by 27 at 10 micromolar (µM) for 0, 3, 6, 12, and 24 hours (h), respectively. Proteins were loaded onto a 10-12% sodium dodecyl sulfatepolyacrylamide gel and then transblotted onto polyvinylidene difluoride membrane. β-Actin was used as an internal control. The fold changes in HO-1 expression are shown on the right at each row using densitometric analyses of the bands. Results are mean±SD (n=3). Bar, standard error; *=$p<0.05$; =$p<0.01$; *=$p<0.001$. All statistical tests are unpaired Student's t test, two-tailed, compared to control (0 h).

Additionally, CCD 841 CoN cells were treated for 3, 6, 12, and 24 h with compound 27 at a fixed dose of 10 µM. As seen in FIG. 4B, 27 significantly increased HO-1 expression from time point of 3 h to 24 h when compared to control (p<0.05 for all time points). These observations demonstrate that derivative 27 increases HO-1 expression in CCD 841 CoN cells in a time-dependent manner.

Chemical Reactivity of Three Representative 6S Derivatives (18, 25, and 27) with L-Cysteine.

It has been observed that reaction of the reactive cysteine residues of Keap1 with electrophiles results in the formation of intermolecular disulfide bridges, thus covalently linking two monomers of Keap1, thereby liberating Nrf2. See Wakabayashi, N., Dinkova-Kostova, A. T., Holtzclaw, W. D., Kang, M. I., Kobayashi, A., Yamamoto, M., Kensler, T. W., and Talalay, P. (2004) "Protection against electrophile and oxidant stress by induction of the phase 2 response: fate of cysteines of the Keap1 sensor modified by inducers." Proc. Natl. Acad. Sci. U.S.A 101, 2040-2045. Natural Nrf2/ARE activators such as xanthohumol, isoliquiritigenin, and SFN, all containing electrophilic groups as Michael acceptor, have been reported to react with the cysteine residues of human Keap1. To understand the underlying mechanisms that the newly synthesized 6S derivatives activate Nrf2, the chemical reactivity of three representative Nrf2 activators (18, 25, and 27) was investigated with L-cysteine in vitro. Michael addition reactions between enone 18 or 27 and L-cysteine occurred immediately under slightly basic condition, thereby in 10 min giving rise to respective cysteine conjugates 35 and 36, both with a cysteine residue attached to the side chain. See Scheme 3A. Regarding catechol compound 25, no Michael addition took place under the same conditions as above perhaps due to the absence of an unsaturated carbonyl entity as a Michael acceptor in the structure. Under oxidative environments (i.e. IBX), reaction between 25 and L-cysteine, however, efficiently produced cysteine conjugate 37, a compound with a cysteine residue binding to the aromatic ring. See Scheme 3A. In addition, treatment of 25 with L-cysteine by tyrosinase from mushroom in PBS generated cysteine conjugate 37 as well.

A)
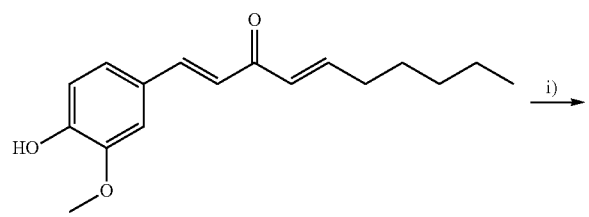
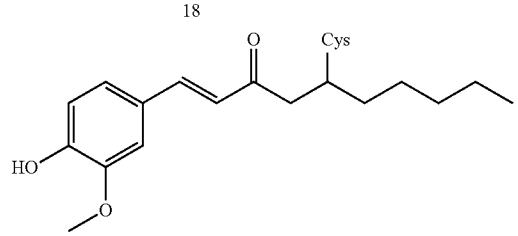
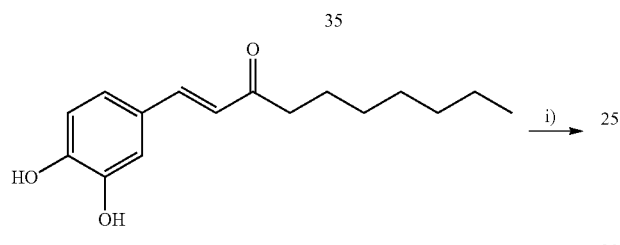
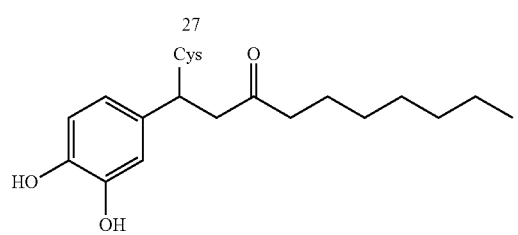
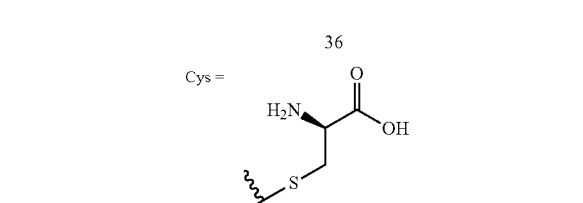
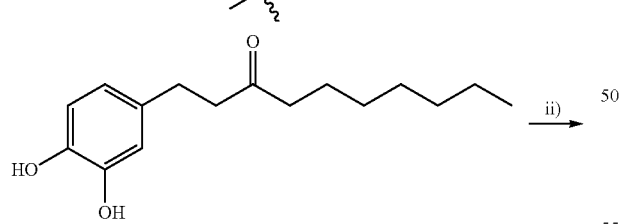
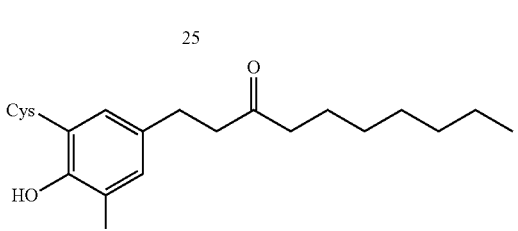
B)
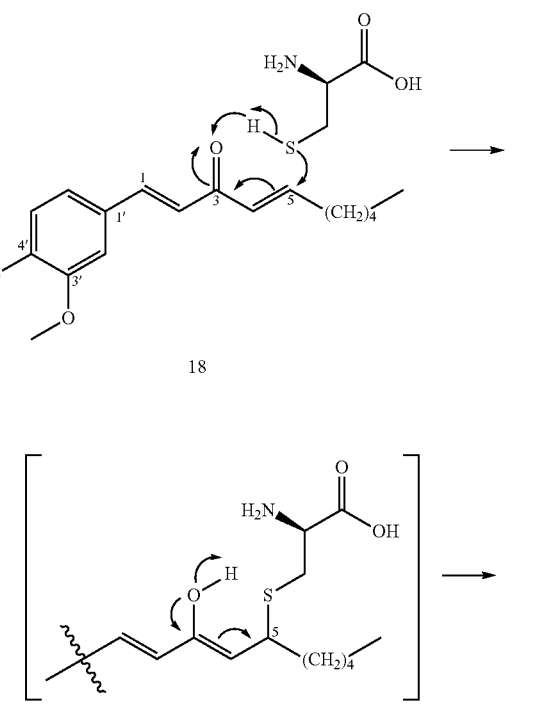
pathway A
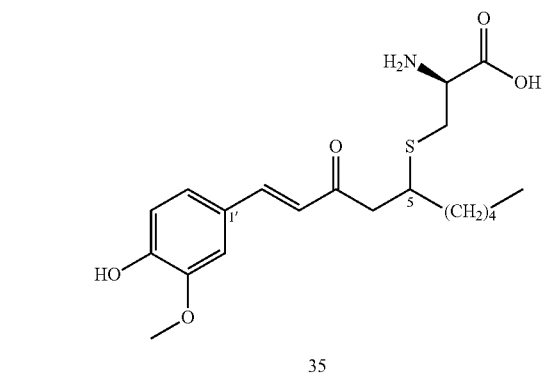
pathway B
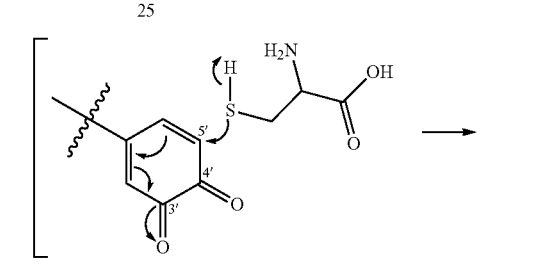

-continued

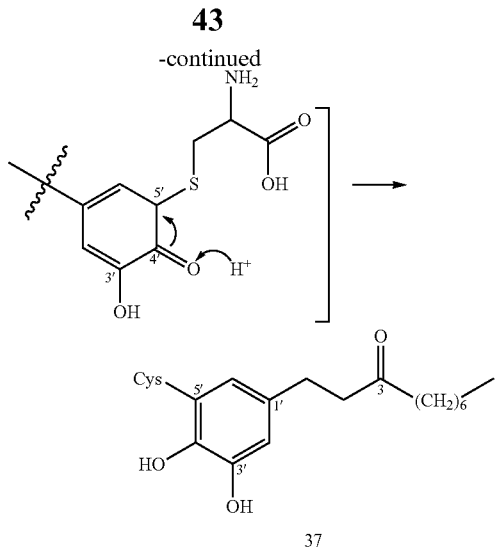

Scheme 3. Synthesis of cysteine conjugates of [6]-shogaol derivatives (35-37) (A) and their proposed reaction mechanism (B). Regents and conditions: i) L-cystein, NaHCO$_3$ (cat.), MeOH/PBS (5:1), rt, 10 min, yield 14-39%; ii) L-cysteine, IBX, MeOH/PBS, -78°C.-rt, 1.5 h, yield 78%.

Without being bound by theory, it is believed that 1) electrophilic alkenes of α,β-unsaturated carbonyl entities in conjugated enones act as Michael acceptors and undergo Michael addition by nucleophilic sulfhydryl groups of cysteine residues under basic conditions, as indicated in pathway A (see Scheme 3B); and 2) high susceptibility of catechol moiety in the structure under oxidative environments leads to the formation of o-quinones as reactive Michael acceptors and subsequently Michael additions take place at ortho-position of the catechol groups by the treatment of cysteine residues, as described in pathway B. See Scheme 3B. As a result, both α,β-unsaturated carbonyl entities and catechol moieties in molecules are believed to act as major active groups for the assaults of the sulfhydryl groups of the cysteine residues.

TABLE 2

Cysteine conjugates found in mice and in zebrafish embryos after treatment of xenobiotics 18 and 25-27, respectively.

| No. | RT (min) | [M + H]$^+$ | MS/MS |
| --- | --- | --- | --- |
| 35 | 22.0 | 396 | 396/378, 275 [M − Cys + H]$^+$ (B) |
| 36 | 21.2 | 384 | 384/263 [M − Cys + H]$^+$ |
| 36a | 22.8 | 386 | 386/265 [M − Cys + H]$^+$ (B), 137 |
| 37 | 24.0 | 384 | 384/367 [M − NH$_2$ + H]$^+$ (B), 295 [M − C$_3$H$_7$NO$_2$ + H]$^+$, 277, 169 |
| 37a | 25.2 | 384 | 384/367, 295 [M − C$_3$H$_7$NO$_2$ + H]$^+$ (B), 267, 167 |
| 37b | 25.1 | 386 | 386/368 [M − H$_2$O + H]$^+$ (B), 351, 297 [M − C$_3$H$_7$NO$_2$ + H]$^+$, 279 |
| 38 | 19.6 | 382 | 382/261 [M − Cys + H]$^+$ |

Cys, cysteine; RT, retention time.

Structural Confirmation of Cysteine Conjugates (35-37) Obtained from the Corresponding Chemical Reaction.

Figures 5A, 5B:
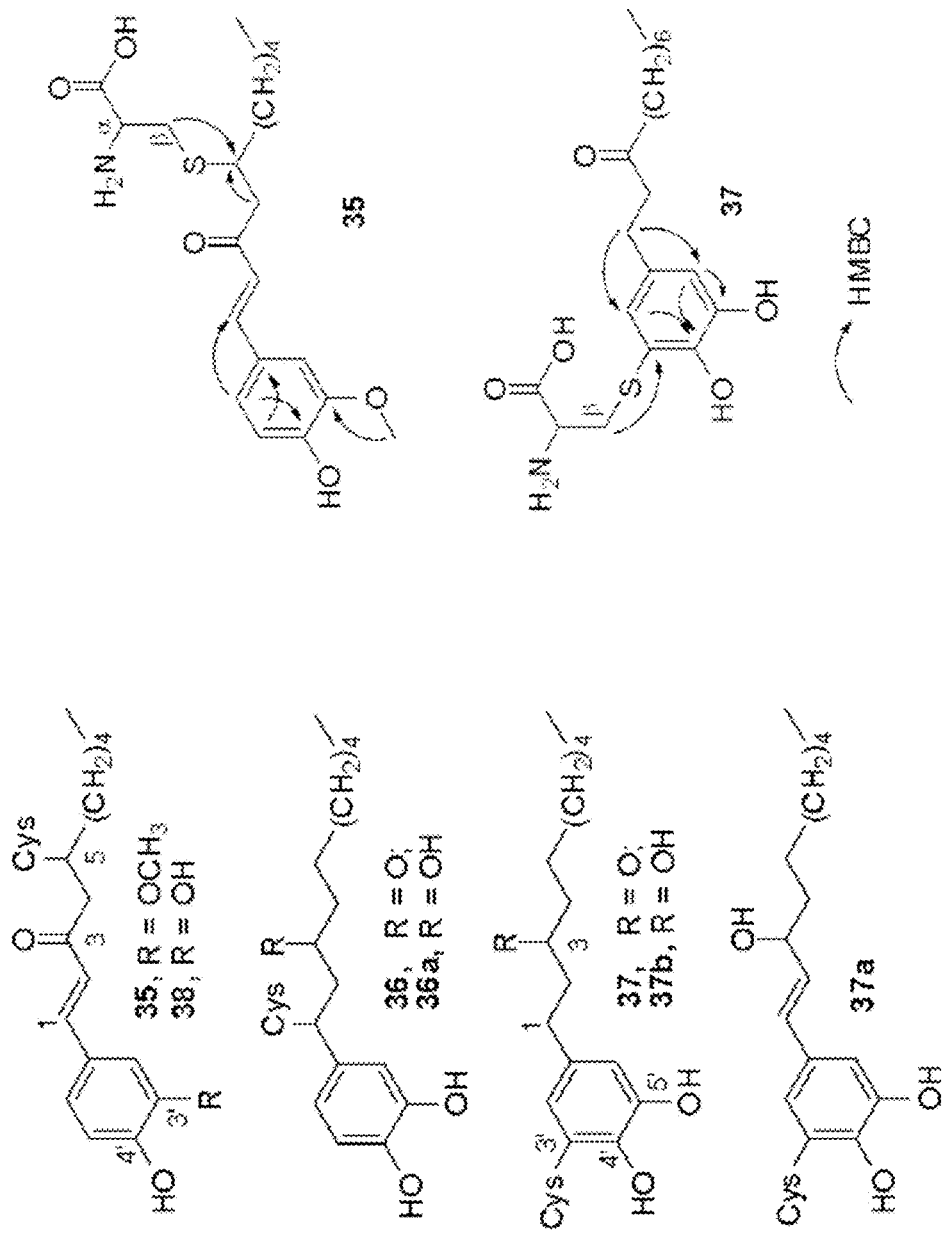
FIG. 5A is a schematic diagram showing the chemical structures of cysteine conjugates 35, 36, 36a, 37, 37a, 37b, and 38 found in mouse urine samples and in zebrafish embryos.
FIG. 5B is a schematic diagram showing the main Heteronuclear Multiple Bond Correlation (HMBC) correlations of structures of conjugates 35 and 37.
Figure 5C:
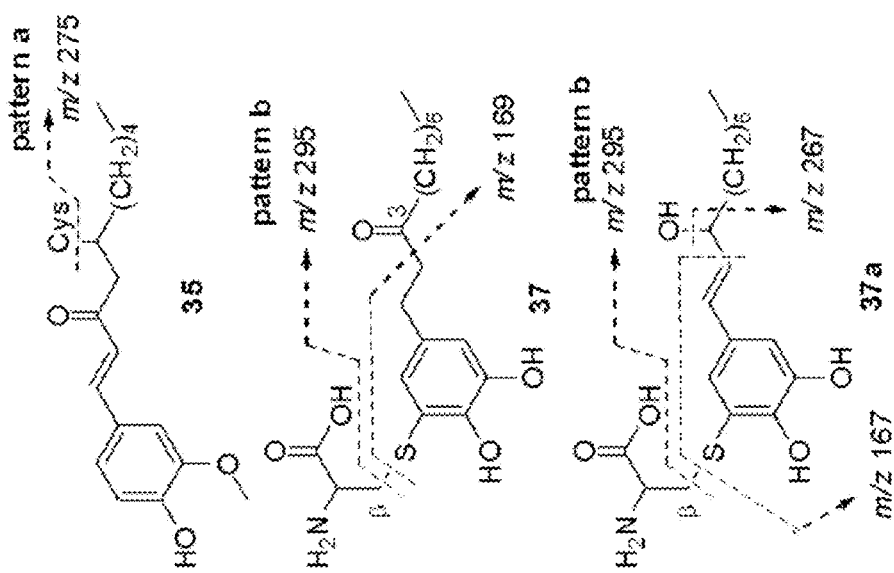
FIG. 5C is a schematic diagram showing the typical fragmentation patterns of conjugates 35, 37, and 37a in their Tandem mass spectrometry (MS/MS) spectra.

Compound 35 was indicated as the cysteine conjugate of dienone 18. The attachment of the cysteine residue at C-5 position in the alkyl tail of 18 was established by HMBC correlations between C-5 (δ$_C$ 42.0) and H$_{Cys}$-β (δ$_H$ 3.22/2.89) and H-6 (δ$_H$ 1.63) as well as H-4 (δ$_H$ 3.36/2.98). See FIG. 5B. This is supported by observing m/z 275 [M-Cys+H]$^+$ (loss of cysteine moiety from m/z 396, pattern a) as the major product ion in its MS/MS spectrum. See Table 2 and FIG. 5C. Therefore, compound 35 was identified as 5-S-cysteinyl-[6]-dehydroparadol. See FIG. 5A. Likewise, the interpretation of NMR data identified 36 as 1-S-cysteinyl-1-(3,4-dihydroxyphenyl)decan-3-one, which was further confirmed by observing m/z 263 [M-Cys+H]$^+$ (loss of cysteine moiety from m/z 384, pattern a) as the major product ion in its MS/MS spectrum. See Table 2. The $^1$H NMR and $^{13}$C NMR spectra of conjugate 37 were similar to those of 36, indicating 37 is a cysteine conjugate of 25. The major differences between 36 and 37 were 1) only two aromatic protons at δ$_H$ 6.82 (1H, brs) and δ$_H$ 6.66 (1H, brs) remained in 37, and 2) signals for thiomethine (—CH—S—) disappeared in 37. This suggested that the cysteine residue in 37 is bound to the aromatic ring rather the alkyl tail. The linkage of the cysteine residue at C-5' position of the catechol moiety was accomplished by HMBC correlations between C-3' (δ$_C$ 119.2) and H$_{Cys}$-β (δ$_H$ 3.47/2.95). See FIG. 5B. This was further supported by its MS/MS fragment ions at m/z 295 originated from the cleavage of C$_{Cys-β}$—S bond (pattern b), and m/z 169 formed by the cleavage of C$_{Cys-β}$—S bond followed by the α-cleavage of carbonyl group between C$_2$-C$_3$ bond. See FIG. 5C. Compound 37 was therefore identified as 3'-S-cysteinyl-1-(3,4-dihydroxyphenyl)decan-3-one. See FIG. 5A.

Formation of Cysteine Conjugates of 18 and 25-27 in Mice and in Zebrafish Embryos.

Figures 6A, 6B:
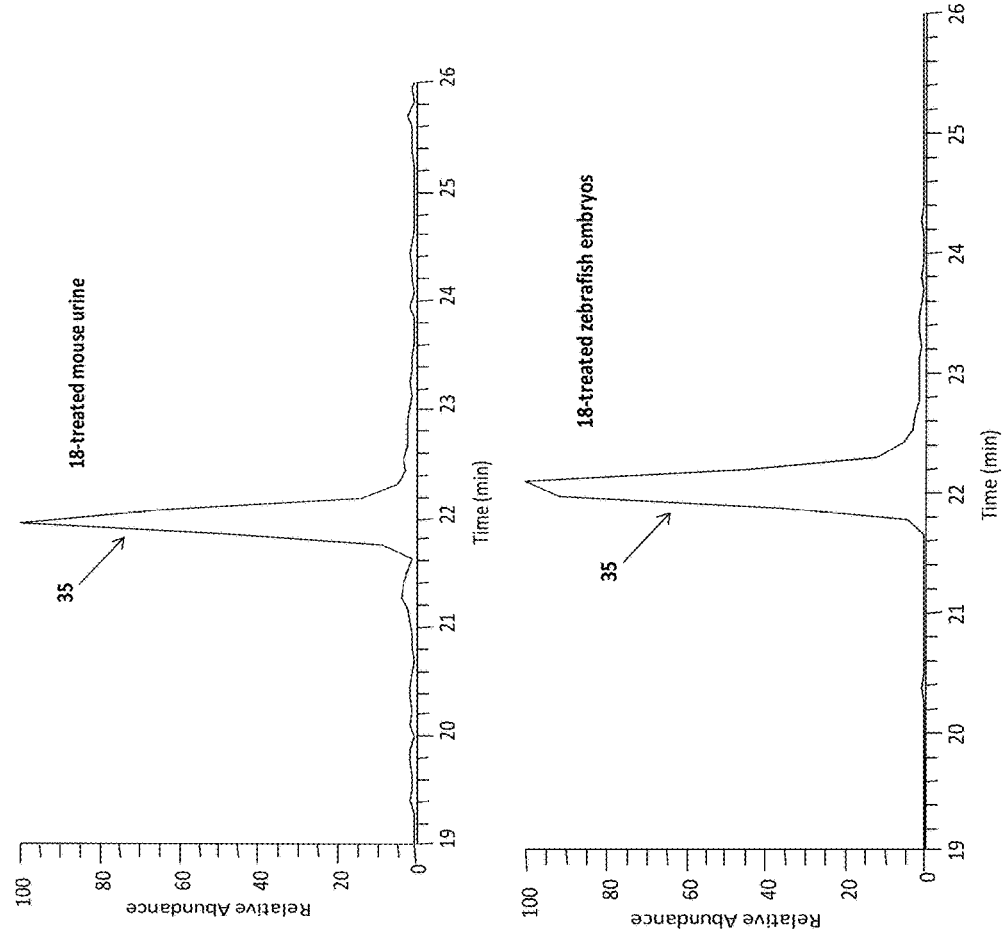
FIG. 6A is a graph showing an extracted ion chromatogram of compound 18-treated mouse urine obtained by positive electrospray ionization mass spectrometry (ESI/MS) interface.
FIG. 6B is a graph showing an extracted ion chromatogram of compound 18-treated zebrafish embryos obtained by positive electrospray ionization mass spectrometry (ESI/MS) interface.
Figure 6C:
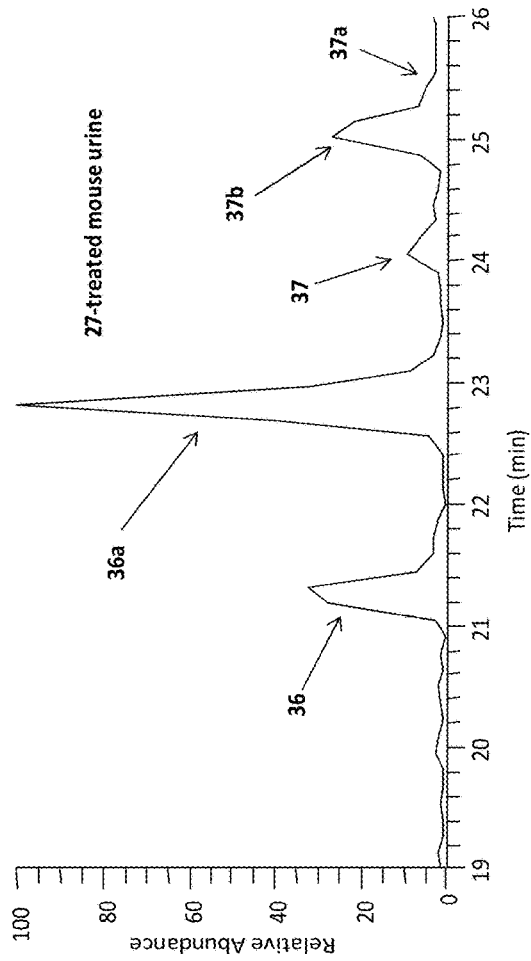
FIG. 6C is a graph showing an extracted ion chromatogram of compound 27-treated mouse urine obtained by positive electrospray ionization mass spectrometry (ESI/MS) interface.
Figure 6D:
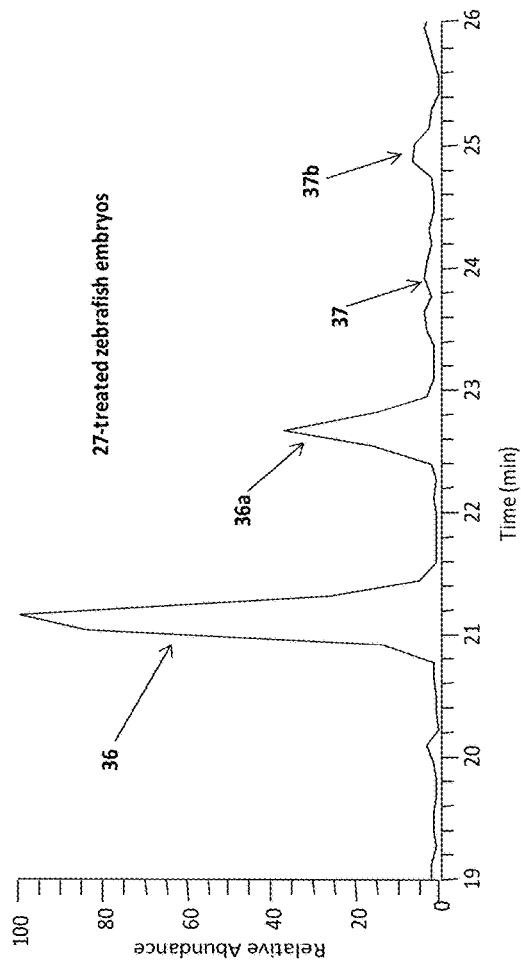
FIG. 6D is a graph showing an extracted ion chromatogram of compound 27-treated zebrafish embryos obtained by positive electrospray ionization mass spectrometry (ESI/MS) interface.

The major active 6S derivatives can bind to the reactive cysteine residues to form related cysteine conjugates in vitro. Compounds 18 and 27 were administrated to mice by oral gavage and 18 and 25-27 were given to zebrafish embryos in incubation medium. Seven cysteine conjugates were identified, including three conjugates (35-37) that have been above identified in vitro and four new analogues (36a, 37a, 37b, and 38), using LC-MS approaches. See FIG. 5A. As shown in FIGS. 6A and 6B, conjugate 35 was predominantly present in both mouse urine and zebrafish embryos after treatment of 18. Besides conjugate 36 and its reduced form 36a, three additional conjugates 37, 37a, and 37b, with cysteine residue binding to the aromatic ring, were detected from 27-treated mouse urine. See FIG. 6C. Likewise, four cysteine conjugates 36, 36a, 37, and 37b were found in 27-treated zebrafish embryos. See FIG. 6D. As expected, conjugates 37 and 37b were exclusively identified in 25-treated zebrafish embryos. See FIG. 6E. Three conjugates 37, 37b, and 38 were detected in 26-treated zebrafish embryos. See FIG. 6F. These in vivo observations demonstrated that 1) unsaturated carbonyl entities in the molecules lead to cysteine conjugation occurring on the alkyl side chain, evidenced by the presence of conjugates 35 in 18-treated mice and zebrafish, 36 and 36a in 27-treated mice and zebrafish, and 38 in 26-treated zebrafish; 2) catechol moieties in the structures induce the binding of cysteine residues to the aromatic rings, evidenced by the appearance of conjugates 37 and 37b in both 25- and 26-treated zebrafish, and 37, 37a, and 37b in 27-treated mice and zebrafish; and 3) coexistence of unsaturated carbonyl entities and catechol moieties in a molecule leads to the formation of both conjugations, evidenced by the existence of conjugates 37, 37b, and 38 in 26-treated zebrafish, and 36, 36a, 37, 37a, and 37b in 27-treated mice and zebrafish. These in vivo results verified that both α,β-unsaturated carbonyl entities and catechol moieties in the molecules act as major active sites for the conjugation with the reactive cysteine residues under physiological conditions.

Structural Elucidation of Cysteine Conjugates (35-38, 36a, 37a and 37b) in Mice and in Zebrafish Embryos by LC/MS.

Figure 6G:
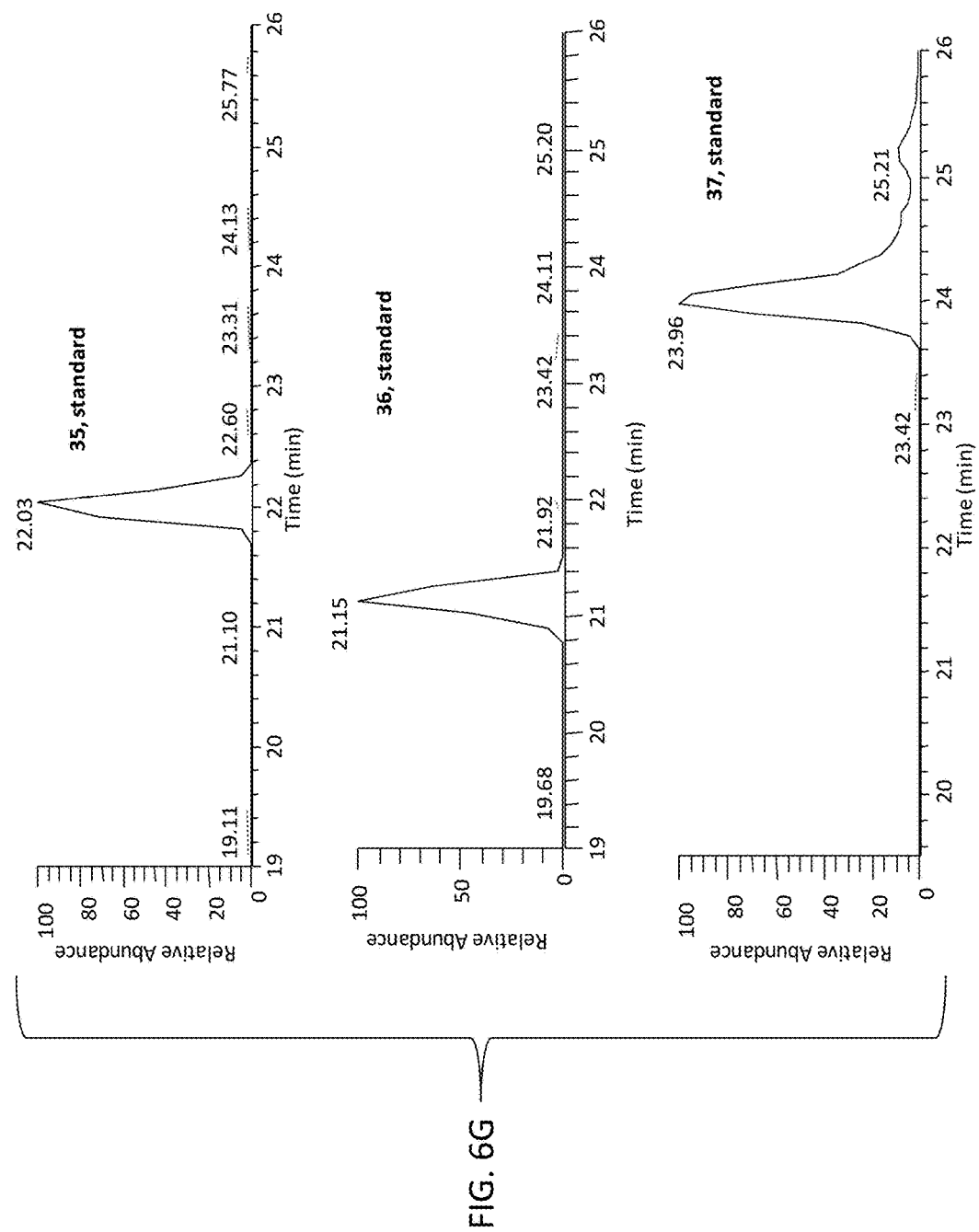
FIG. 6G is a set of graphs showing the extracted ion chromatograms of authentic standards of compound 35 (top), compound 36 (middle), and compound 37 (bottom) obtained by positive electrospray ionization mass spectrometry (ESI/MS) interface.
Figure 7A:
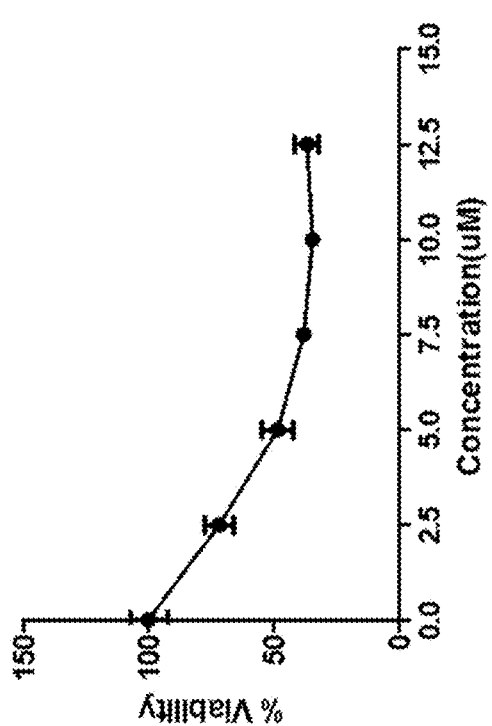
FIG. 7A is a graph of the inhibitory effects of compound M14-11 on the growth of human colon cancer cells (HCT-116). Cells were treated with 2.5, 5.0, 7.5, 10.0, or 12.5 micromolar (µM) concentrations of the compound for 24 hours in the presence of 10 percent (%) fetal bovine serum (FBS) and 1% streptomycin/penicillin at 37 degrees Celsius (° C.). Bar, standard error (n=6). The 50% inhibitory concentration ($IC_{50}$) value is expressed as the mean±SD (n=6).
Figure 7B:
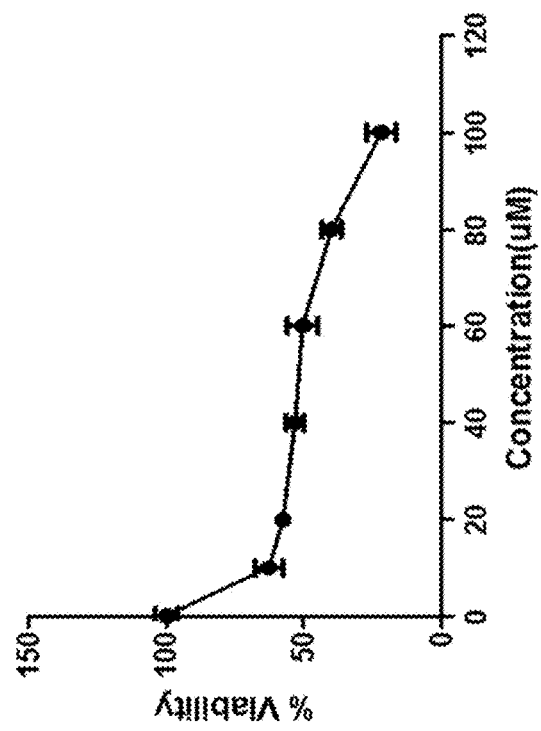
FIG. 7B is a graph of the inhibitory effects of compound M14-13 on the growth of human colon cancer cells (HCT-116). Cells were treated with 10, 20, 40, 60, 80, or 100 micromolar (µM) concentrations of the compound for 24 hours in the presence of 10 percent (%) fetal bovine serum (FBS) and 1% streptomycin/penicillin at 37 degrees Celsius (° C.). Bar, standard error (n=6). The 50% inhibitory concentration ($IC_{50}$) value is expressed as the mean±SD (n=6).
Figure 7C:
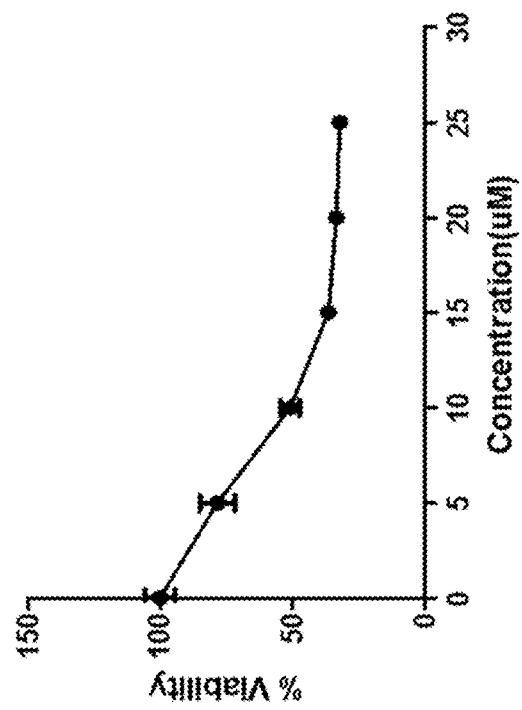
FIG. 7C is a graph of the inhibitory effects of compound M14-11 on the growth of human colon cancer cells (HT-29). Cells were treated with 5, 10, 15, 20, or 25 micromolar (µM) concentrations of the compound for 24 hours in the presence of 10 percent (%) fetal bovine serum (FBS) and 1% streptomycin/penicillin at 37 degrees Celsium (° C.). Bar, standard error (n=6). The 50% inhibitory concentration ($IC_{50}$) value is expressed as the mean±SD (n=6).
Figure 7D:
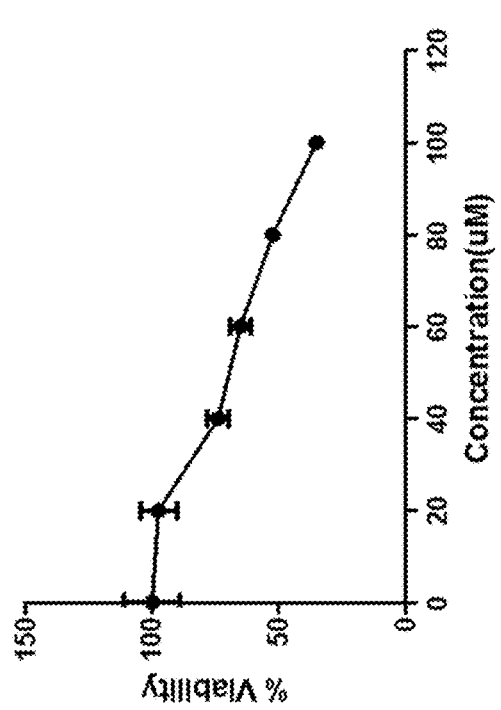
FIG. 7D is a graph of the inhibitory effects of compound M14-13 on the growth of human colon cancer cells (HT-29). Cells were treated with 20, 40, 60, 80, or 100 micromolar (µM) concentrations of the compound for 24 hours in the presence of 10 percent (%) fetal bovine serum (FBS) and 1% streptomycin/penicillin at 37 degrees Celsius (° C.). Bar, standard error (n=6). The 50% inhibitory concentration ($IC_{50}$) value is expressed as the mean±SD (n=6).

The presence of conjugates 35-37 in mice and in zebrafish embryos was confirmed by comparison of their retention times and MS/MS fragmentation patterns to those of authentic references obtained from the chemical reactions between corresponding 6S derivatives and L-cysteine. See Table 2 and FIG. 6G. The molecular ion of 36a at m/z 386 [M+H]$^+$ was two units higher than that of 36, indicating 36a is the reduced form of 36. Major fragment ion at m/z 265/386 [M-Cys+H]$^+$ in its MS/MS spectrum (see Table 2), corresponding to the loss of a cysteine moiety from parent ion at m/z 386 (pattern A), suggests that 36a is 1-S-cysteinyl-1-(3,4-dihydroxyphenyl)decan-3-ol. See FIG. 5A. Compound 37a had a same molecular ion at m/z 384 [M+H]$^+$ (263+121) to that of 37, indicating 37a is an isomer of 37. The major MS/MS fragment ion at m/z 295 in 37a, originating from the cleavage of $C_{Cys-\beta}$—S bond (pattern B), demonstrated the cysteine residue in 37a is bound to the aromatic ring. See FIG. 5C. Fragment at m/z 167 in 37a, forming by the cleavage of $C_{Cys-\beta}$—S bond followed by the α-cleavage of carbonyl group between $C_2$-$C_3$ bond, was two units less than ion at m/z 169 in 37, suggesting an extra double bond is present in 37a. This was also supported by ion peak at m/z 267, corresponding to the α-cleavage of hydroxyl group between $C_3$-$C_4$ bond followed by a loss of $H_2O$. See FIG. 5C. Taken together, compound 37a was proposed as an allyl alcohol isomer of 37, 3'-S-cysteinyl-1-(4,5-dihydroxyphenyl)decen-3-ol. See FIG. 5A. The molecular weight of compound 37b (m/z 386 [M+H]$^+$) is two units higher than that of 37, indicating 37b is a reduced product of 37. The major MS/MS fragment at m/z 297, corresponding to the cleavage of $C_{Cys-\beta}$—S bond (pattern b) (see Table 2), suggested that cysteine residue in 37b is attached at the aromatic ring. Thus, compound 37b was tentatively proposed to have the structure of 3'-S-cysteinyl-1-(4,5-dihydroxyphenyl)decan-3-ol. See FIG. 5A. Compound 38, found in 26-treated zebrafish embryos (see FIG. 6F), had a molecular ion at m/z 382 [M+H]$^+$ (261+121), indicating 38 is a cysteine conjugate of 26. The major MS/MS fragment ion at m/z 261 (lose of cysteine moiety from m/z 382, pattern a) (see Table 2) suggested 38 is 5-S-cysteinyl-1-(3,4-dihydroxyphenyl)decen-3-one. See FIG. 5A.

Growth Inhibitory Effects of 26 (M14-11) and 27 (M14-13) Against Human Colon Cancer Cells.

Both compounds 26 and 27 can effectively inhibit the growth of human colon cancer cells HCT-116 and HT-29 in a dose-dependent manner, respectively. See FIGS. 7A-7D. However, compound 26 exerted greater potentials in both cancer cell lines (HCT-116: $IC_{50}$=5.42 μM; and HT-29: $IC_{50}$=11.49 μM) than 27 (HCT-116: $IC_{50}$=34.13 μM; and HT-29: $IC_{50}$=78.36 μM). Without being bound to any one theory, this suggested that an extra conjugated double bond in side chain favors the toxicities against colon cancer growth.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A compound having a structure of the formula:

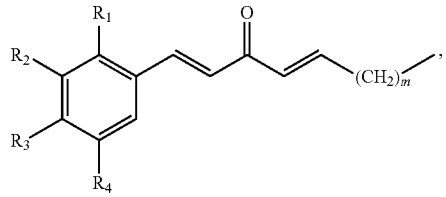

wherein:
m is an integer between 0 and 4;
$R_1$ is —H, halogen, halogen-substituted $C_1$-$C_4$ alkoxy, —COOH, or halogen-substituted $C_1$-$C_4$ alkyl;
$R_2$ is —H, halogen, —OH, halogen-substituted $C_1$-$C_4$ alkoxy, —COOH, or halogen-substituted $C_1$-$C_4$ alkyl; and
$R_3$ and $R_4$ are independently selected from the group consisting of —H, —OH, amino, $C_1$-$C_4$ alkyl, $C_1$-$C_4$ alkylamino, and $C_1$-$C_4$ alkoxy, subject to the proviso that (a) when $R_1$ and $R_2$ are each H, (i) $R_3$ is selected from hydroxyl and $C_1$-$C_4$ alkoxy and $R_4$ is selected from OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$, and $R_1$ is —F;
or a pharmaceutically acceptable salt thereof.

2. The compound of claim 1, wherein m is 0, 2 or 4.

3. The compound of claim 2, wherein m is 4.

4. The compound of claim 2, wherein $R_3$ and $R_4$ are each independently selected from the group consisting of —H, —OH, and $C_1$-$C_4$ alkoxy, subject to the proviso that (a) when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy; and (b) when $R_4$ is —H, $R_3$ is —H, $R_2$ is —$CF_3$, and $R_1$ is —F.

5. The compound of claim 2, wherein
$R_1$ is —H, —F, —$OCF_3$, —$OCHF_2$, —COOH, or —$CF_3$; and
$R_2$ is —H, —F, —OH, —$OCF_3$, —$OCHF_2$, —COOH, or —$CF_3$.

6. A compound having a structure of the formula:

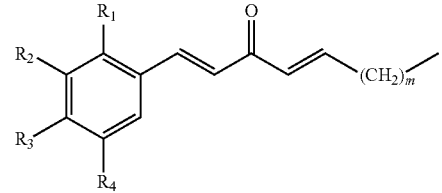

wherein:
m is 0, 2, or 4;
$R_1$ is —H;
$R_2$ is selected from the group consisting of —H, —F, —OH, and —$CF_3$; and
$R_3$ and $R_4$ are independently selected from the group consisting of —OH and $C_1$-$C_4$ alkoxy, subject to the proviso that when $R_1$ and $R_2$ are each —H, (i) $R_3$ is selected from hydroxyl and $C_1$-$C_4$ alkoxy and $R_4$ is selected from —OH and $C_2$-$C_4$ alkoxy or (ii) $R_3$ is $C_1$-$C_4$ alkoxy and $R_4$ is selected from —OH and $C_1$-$C_4$ alkoxy.

7. The compound of claim 5, wherein $R_2$ is —F, —OH, or $CF_3$; and $R_3$ and $R_4$ are independently selected from —OH and $C_1$-$C_4$ alkoxy.

8. The compound of claim 7, wherein $R_2$ is —F or $CF_3$; and $R_3$ and $R_4$ are independently selected from —OH, methoxy, isopropoxy, and tert-butoxy.

9. The compound of claim 1, wherein the compound is selected from the group consisting of:

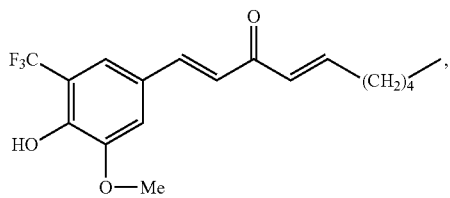

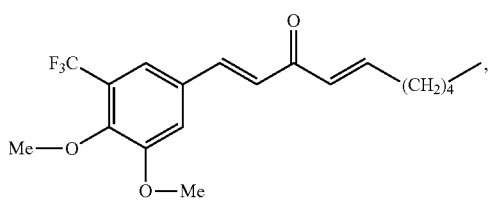

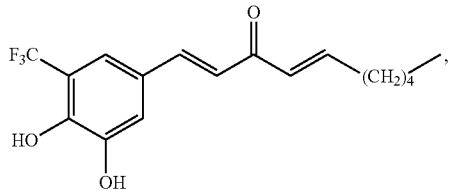

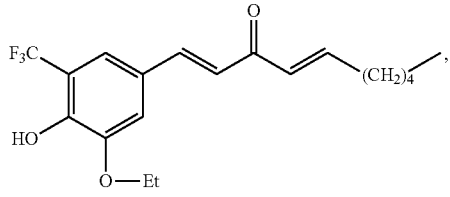

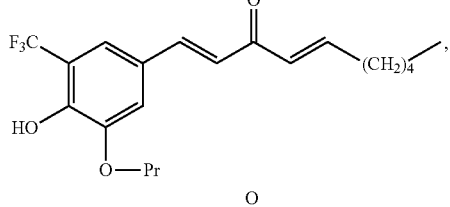

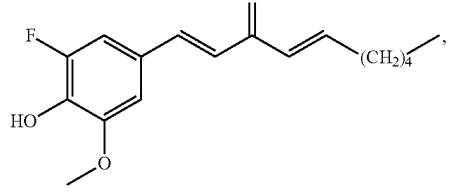

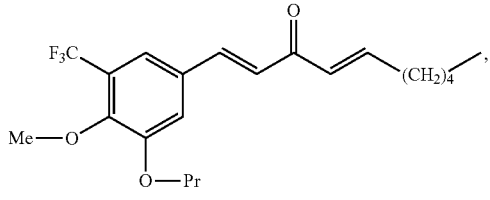

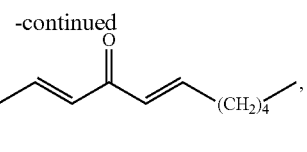

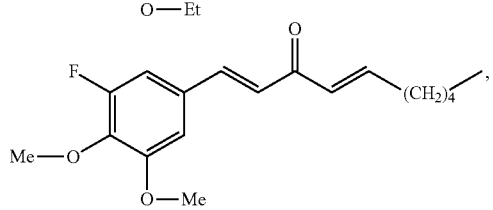

and pharmaceutically acceptable salts thereof.

10. The compound of claim 1, wherein the compound is selected from the group consisting of:

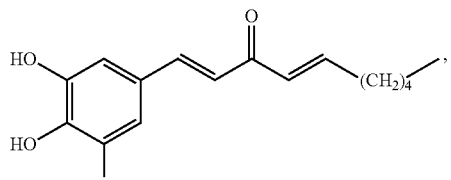

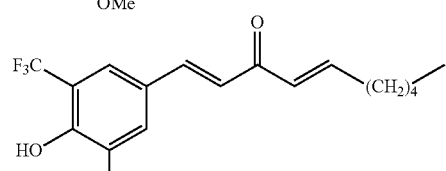

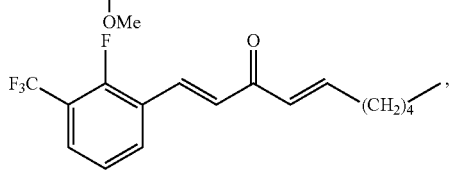

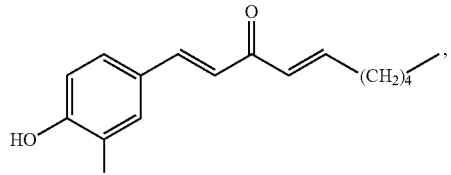

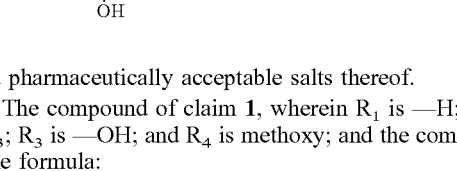

and pharmaceutically acceptable salts thereof.

11. The compound of claim 1, wherein $R_1$ is —H; $R_2$ is —$CF_3$; $R_3$ is —OH; and $R_4$ is methoxy; and the compound has the formula:

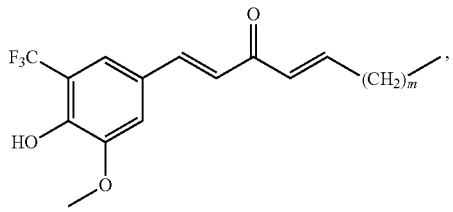

wherein m is 0, 2, or 4.

12. A pharmaceutical composition comprising a compound of claim 1, and a pharmaceutically acceptable carrier.

13. The pharmaceutical composition of claim 12, wherein m is 0, 2, or 4.

14. The pharmaceutical composition of claim 13, wherein

R$_1$ is —H, —F, —OCF$_3$, —OCHF$_2$, —COOH, or —CF$_3$; and

R$_2$ is —H, —F, —OH, —OCF$_3$, —OCHF$_2$, —COOH, or —CF$_3$.

15. A pharmaceutical composition comprising a compound of claim 6, and a pharmaceutically acceptable carrier.

16. The pharmaceutical composition of claim 14, wherein R$_2$ is —F, —OH, or CF$_3$; and R$_3$ and R$_4$ are independently selected from —OH and C$_1$-C$_4$ alkoxy.

17. The pharmaceutical composition of claim 12, wherein the compound is selected from the group consisting of:

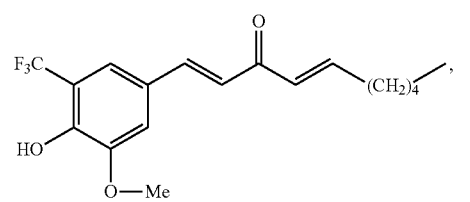

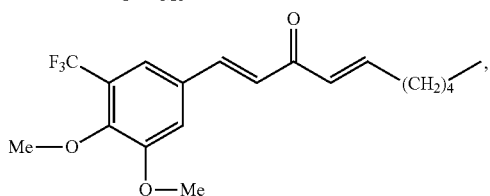

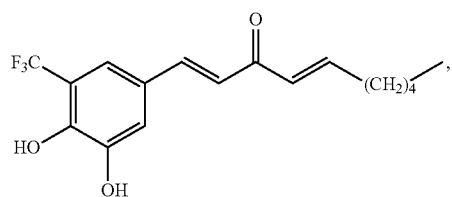

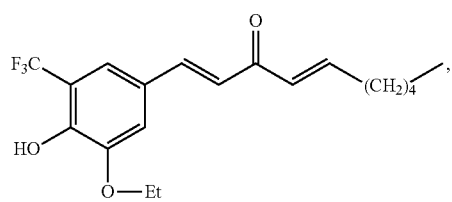

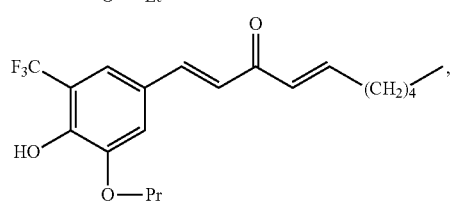

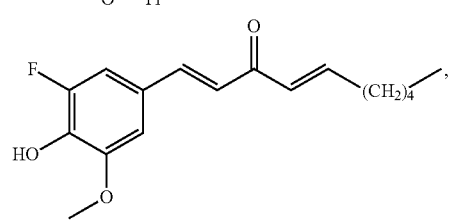

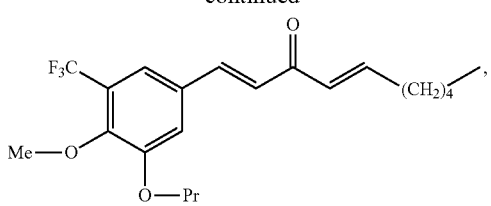

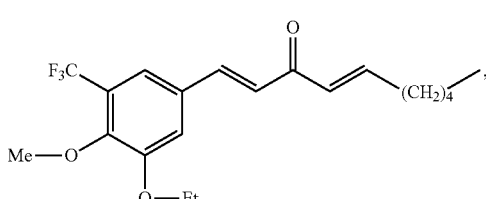

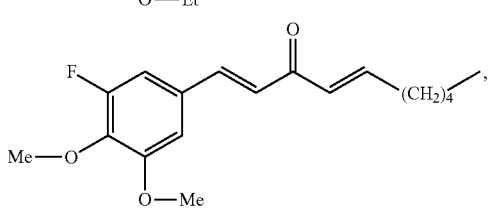

and pharmaceutically acceptable salts thereof.

18. The pharmaceutical composition of claim 12, wherein the compound is selected from the group consisting of:

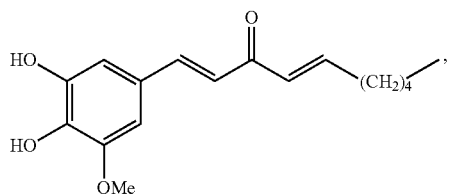

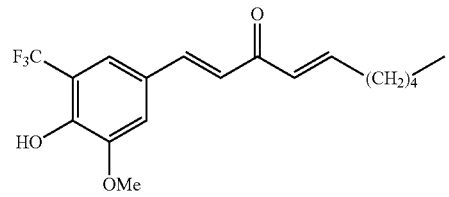

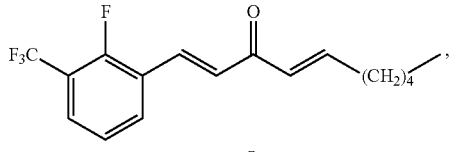

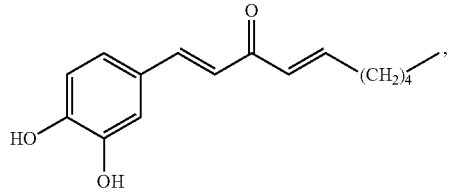

and pharmaceutically acceptable salts thereof.

19. The pharmaceutical composition of claim 12, wherein R$_1$ is —H; R$_2$ is —CF$_3$; R$_3$ is —OH; and R$_4$ is methoxy; and the compound has a structure of the formula:

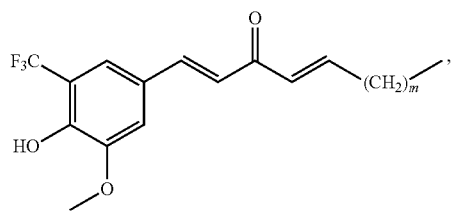
wherein m is 0, 2, or 4.
* * * * *